US010765779B2

(12) United States Patent
Crawford-Corrie et al.

(10) Patent No.: US 10,765,779 B2
(45) Date of Patent: Sep. 8, 2020

(54) MEDICAL IMPLANT

(71) Applicant: The University of Sheffield, Sheffield (GB)

(72) Inventors: Aileen Crawford-Corrie, Sheffield (GB); David John Buttle, Sheffield (GB); John William Haycock, Sheffield (GB)

(73) Assignee: THE UNIVERSITY OF SHEFFIELD, South Yorkshire (GB)

( * ) Notice: Subject to any disclaimer, the term of this patent is extended or adjusted under 35 U.S.C. 154(b) by 0 days.

(21) Appl. No.: 15/747,410

(22) PCT Filed: Jul. 25, 2016

(86) PCT No.: PCT/GB2016/052270
§ 371 (c)(1),
(2) Date: Jan. 24, 2018

(87) PCT Pub. No.: WO2017/017425
PCT Pub. Date: Feb. 2, 2017

(65) Prior Publication Data
US 2018/0214613 A1 Aug. 2, 2018

(30) Foreign Application Priority Data
Jul. 24, 2015 (GB) .................................. 1513097.4

(51) Int. Cl.
| | | |
|---|---|---|
| *A61L 27/54* | (2006.01) | |
| *A61F 2/30* | (2006.01) | |
| *A61L 27/18* | (2006.01) | |
| *A61L 27/34* | (2006.01) | |
| *A61L 27/56* | (2006.01) | |
| *A61L 27/20* | (2006.01) | |
| *A61K 47/64* | (2017.01) | |
| *A61K 38/18* | (2006.01) | |

(52) U.S. Cl.
CPC .......... *A61L 27/54* (2013.01); *A61F 2/30756* (2013.01); *A61K 38/1841* (2013.01); *A61K 47/642* (2017.08); *A61L 27/18* (2013.01); *A61L 27/20* (2013.01); *A61L 27/34* (2013.01); *A61L 27/56* (2013.01); *A61F 2002/30677* (2013.01); *A61F 2002/30766* (2013.01); *A61L 2300/414* (2013.01); *A61L 2300/608* (2013.01); *A61L 2430/02* (2013.01); *A61L 2430/06* (2013.01); *A61L 2430/24* (2013.01)

(58) Field of Classification Search
CPC .......................... A61K 47/642; A61K 38/1841
See application file for complete search history.

(56) References Cited

U.S. PATENT DOCUMENTS

| | | | | |
|---|---|---|---|---|
| 2006/0067969 | A1* | 3/2006 | Lu ................. | A61L 27/3839 424/423 |
| 2010/0247651 | A1* | 9/2010 | Kestler .......... | A61K 38/1858 424/484 |
| 2013/0251683 | A1 | 9/2013 | Santos et al. | |

FOREIGN PATENT DOCUMENTS

| | | |
|---|---|---|
| CN | 101269240 | 9/2008 |
| WO | WO 2004/040308 A1 | 5/2004 |
| WO | WO 2012/113812 A1 | 8/2012 |
| WO | WO 2014/153610 A1 | 10/2014 |

OTHER PUBLICATIONS

International Search Report and the Written Opinion of the International Searching Authority corresponding to International Patent Application No. PCT/GB2016/052270 (11 pages) (dated Sep. 30, 2016).
Search Report under Section 17(5) corresponding to GB Application No. 1513097.4 (4 pages) (dated Feb. 26, 2016).
Abramson et al. "Prospects for disease modification in osteoarthritis" *Nature Clinical Practice. Rheumatology* 2(6):304-312 (2006) (Abstract only).
Abramson et al. "Developments in the scientific understanding of osteoarthritis" *Arthritis Research & Therapy* 11:227-236 (2009).
Aggarwal et al. "Revision Total Knee Arthroplasty in the Young Patient: Is There Trouble on the Horizon?" *The Journal of Bone & Joint Surgery* 96(7):536-542 (2014).
Brown et al. "Cooperative Heparin-Mediated Oligomerization of Fibroblast Growth Factor-1 (FGF1) Precedes Recruitment of FGFR2 to Ternary Complexes" *Biophysical Journal* 104:1720-1730 (2013).
Chen et al. "Thermal Stability of Fibroblast Growth Factor Protein Is a Determinant Factor in Regulating Self-Renewal, Differentiation, and Reprogramming in Human Pluripotent Stem Cells" *Stem Cells* 30(4):623-630 (2012).
Chen et al. "Layer-by-layer assembly of chitosan stabilized multilayered liposomes for paclitaxel delivery" *Carbohydrate Polymers* 111:298-304 (2014) (Abstract only).
Clar et al. "Clinical and cost-effectiveness of autologous chondrocyte implantation for cartilage defects in knee joints: systematic review and economic evaluation" *Health Technology Assessment* 9(47):1-98 (2005).
Crawford et al. "Chondrocyte Isolation, Expansion, and Culture on Polymer Scaffolds" *Methods in Molecular Biology* 238:147-158 (2004).

(Continued)

*Primary Examiner* — Kyle A Purdy
(74) *Attorney, Agent, or Firm* — Myers Bigel, P.A.

(57) ABSTRACT

The present invention relates to a cell-free, multi-layered medical device having bespoke, multifunctional bioactivity for the purpose of regeneration of skeletal tissues. The medical device may actively promote homing of stem cells into the medical device and promote their differentiation into the required cell type and promote de-novo tissue formation. The invention includes methods of making the medical device, uses of the medical device in promoting regeneration of the articular cartilage of a joint surface and in promoting healing and regeneration of skeletal tissues, for example, meniscal cartilage, tendon and ligament tissues and also healing of bone tissue indications such as fractures.

21 Claims, 18 Drawing Sheets

(56) References Cited

OTHER PUBLICATIONS

Farndale et al. "Improved quantitation and improved discrimination of sulphated glycosaminoglycans by use of dimethylmethylene blue" *Biochimia et Biphysica Acta* 883(2):173-177 (1986) (Abstract only).

Fisher, John "Surgery for Arthritis: Total Hip and Knee Joint Replacement" *Reports on the Rheumatic Diseases Series 5: Topical Reviews* 3:1-8 (2004).

Freeman et al. "The influence of sequential delivery of angiogenic factors from affinity-binding alginate scaffolds on vascularization" *Biomaterials* 30(11):2122-2131 (2009) (Abstract only).

Gidwani et al. "The orthopaedic approach to managing osteoarthritis of the knee" *The BMJ* 329:1220-1224 (2004).

Goldring et al. "Osteoarthritis" *Journal of Cellular Physiology* 213:626-634 (2007).

Hileman et al. "Glycosaminoglycan-protein interactions: definition of consensus sites in glycosaminoglycan binding proteins" *Bioassays* 20(2):156-167 (1998) (Abstract only).

International Preliminary Report on Patentability corresponding to International Patent Application No. PCT/GB2016/052270 (8 pages) (dated Jan. 30, 2018).

Jones et al. "Synovial Fluid Mesenchymal Stem Cells in Health and Early Osteoarthritis" *Arthritis & Rheumatism* 58(6):1731-1740 (2008).

Kim et al. "Extracellular matrix and cell signalling: the dynamic cooperation of integrin, proteoglycan and growth factor receptor" *Journal of Endocrinology* 209:139-151 (2011).

Kim et al. "Causes of Failure after Total Knee Arthroplasty in Osteoarthritis Patients 55 Years of Age or Younger" *Knee Surgery & Related Research* 26(1):13-19 (2014).

Knox et al. "Perlecan: how does one molecule do so many things?" *Cellular and Molecular Life Sciences* 63:2435-2445 (2006).

Kufareva et al. "Chemokine and chemokine receptor structure and interactions: implications for therapeutic strategies" *Immunology & Cell Biology* 93(4):372-383 (2015).

Laguri et al. "Relationships between glycosaminoglycan and receptor binding sites in chemokines—the CXCL12 example" *Carbohydrate Research* 343(12):2018-2023 (2008) (Abstract only).

Laupattarakasem et al. "Arthroscopic debridement for knee osteoarthritis" *Cochrane Database of Systematic Reviews* 1(CD005118) (3 pages) (2008).

Leardini et al. "Direct and indirect costs of osteoarthritis of the knee" *Clinical and Experimental Rheumatology* 22:699-706 (2004).

Lortat-Jacob, H. "The molecular and functional implications of chemokine interactions with heparin sulphate" *Current Opinion in Structural Biology* 19(5):543-548 (2009) (Abstract only).

Lutolf et al. "Synthetic biomaterials as instructive microenvironments for morphogenesis in tissue engineering" *Nature Biotechnology* 23(1):47-55 (2005) (Abstract only).

Lyon et al. "The Interaction of the Transforming Growth Factor—as with Heparin/Heparan Sulfate Is Isoform-specific" *The Journal of Biological Chemistry* 272(29):18000-18006.

Mahoney et al. "A method for the immobilization of heparin to surfaces" *Analytical Biochemistry* 330(1):123-129 (2004) (Abstract only).

Manakhov et al. "Deposition of stable amine coating onto polycaprolactone nanofibers by low pressure cyclopropylamine plasma polymerization" *Thin Solid Films* 581:7-13 (2015) (Abstract only).

Mccaffrey et al. "Transforming growth factor-beta 1 is a heparin-binding protein: identification of putative heparin-binding regions and isolation of heparins with varying affinity for TGF-beta 1" *Journal of Cellular Physiology* 152(2):430-440 (1992) (Abstract only).

Messner et al. "Cartilage repair: A critical review" *Acta Orthopaedica Scandinavica* 67(5):523-529 (1996).

Minas et al. "Advanced techniques in autologous chondrocytes transplantation" *Clinics in Sports Medicine* 18(1):13-44 (1999) (Abstract only).

Peterson et al. "Two to 9-year outcome after autologous chondrocyte transplantation" *Clinical Orthopaedics and Related Research* 374:212-234 (2000) (Abstract only).

Pomin et al. "Current structural biology of the heparin interactome" *Current Opinion in Structural Biology* 34:17-25 (2015) (Abstract only).

Proudfoot et al. "Glycosaminoglycan binding and oligomerization are essential for the in vivo activity of certain chemokines" *Proceedings of the National Academy of Sciences* 100(4):1885-1890 (2003).

Raman et al. "Structural Insights into Biological Roles of Protein-Glycosaminoglycan Interactions" *Chemistry & Biology* 12:267-277 (2005).

Rapraeger, Alan C. "Syndecan-regulated Receptor Signaling" *The Journal of Cell Biology* 149(5):995-997 (2000).

Rider, CC "Heparin/heparan sulphate binding in the TGF-beta cytokine superfamily" *Biochemical Society Transactions* 34(Pt. 3):458-460 (2006) (Abstract only).

Robinson et al. "Surface Gradient of Functional Heparin" *Advanced Materials* 20:1166-1169 (2008).

Robinson et al. "Glycosaminoglycan (GAG) surfaces for characterizing GAG-protein interactions" *Biomaterials* 33(4):1007-1016 (2012) (Abstract only).

Roos, EM "Joint injury causes knee osteoarthritis in young adults" *Current Opinion in Rheumatology* 17(2):195-200 (2005) (Abstract only).

Ruano-Ravina et al. "Autologous chondrocyte implantation: a systemic review" *Osteoarthritis & Cartilage* 14:47-51 (2006).

Sampson et al. "Autologous bone marrow concentrate: review and application of a novel intra-articular orthobiologic for cartilage disease" *The Physician and Sportsmedicine* 41(3):7-18 (2013) (Abstract only).

Simon et al. "Articular cartilage injury pathways and treatment options" *Sports Medicine and Arthroscopy* 14(3):146-154 (2006) (Abstract only).

Steadman et al. "Microfracture: surgical technique and rehabilitation to treat chondral defects" *Clinical Orthopaedics and Related Research* 391(Suppl):5362-5369 (2001) (Abstract only).

Stoll et al. "The extracellular human melanoma inhibitory activity (MIA) protein adopts an SH3 domain-like fold" *The EMBO Journal* 20(3):340-349 (2001).

Sun et al. "Self-organization of skin cells in three-dimensional electrospun polystyrene scaffolds" *Tissue Engineering* 11(7-8):1023-1033 (2005) (Abstract only).

Taguchi et al. "Apatite formation on/in hydrogel matrices using an alternative soaking process: II. Effect of swelling ratios of poly(vinyl alcohol) hydrogel matrices on apatite formation" *Journal of Biomaterials Science, Polymer Edition* 10(3):331-339 (1999) (Abstract only).

Trattnig et al. "Matrix-based autologous chondrocytes implantation for cartilage repair: noninvasive monitoring by high-resolution magnetic resonance imaging" *Magnetic Resonance Imaging* 23(7):779-787 (2005) (Abstract only).

Tscheudschilsuren et al. "Regulation of stem cell and chondrocyte differentiation by MIA" *Experimental Cell Research* 312(1):63-72 (2006) (Abstract only).

Van Der Kraan et al. "Interaction of chondrocytes, extracellular matrix and growth factors: relevance for article cartilage tissue engineering" *Osteoarthritis & Cartilage* 10:631-637 (2002).

Volpato et al. "Preservation of FGF-2 bioactivity using heparin-based nanoparticles, and their delivery from electrospun chitosan fibers" *Acta Biomaterialia* 8:1551-1559 (2012).

Vulic et al. "Tunable Growth Factor Delivery from Injectable Hydrogels for Tissue Engineering" *Journal of the American Chemical Society* 134(2):882-885 (2011) (Abstract only).

Wasiak et al. "Autologous cartilage implantation for full thickness cartilage defects of the knee" *Cochrane Database of Systemic Reviews* 3:CD003323 (2006) (Abstract only).

Xu et al. "Heparin-decorated, hyaluronic acid-based hydrogel particles for the controlled release of bone morphogenetic protein 2" *Acta Biomaterialia* 7(8):3050-3059 (2011).

(56) References Cited

OTHER PUBLICATIONS

Yasuda et al. "Biomedical applications of plasma polymerization and plasma treatment of polymer surfaces" *Biomaterials* 3(2):68-77 (1982) (Abstract only).
Zern et al. "Control Growth Factor Release Using a Self-Assembled [polycation:heparin] Complex" *PLoS One* 5(6):e11017 (2010).
Bragg et al. "Stromal cell-derived factor-1 as a potential therapeutic target for osteoarthritis and rheumatoid arthritis" Therapeutic Adv in Chronic Dis., 10:1-10 2019.
Hintze et al. "Sulphated hyaluronan and chondroitin sulphate derivatives interact differently with human transforming factor-$\beta$1 (TGF-$\beta$1)" Acta Biomaterialia, 8:2144-2152 2012
Lyon et al. "The interactions of transforming growth factor beta with heparin/heparin sulphate is isoform-specific" J Biol Chem. 272(29):18000-18006 1997.
Rider et al. "Heparin, heparan sulphate and the TGF-beta cytokine superfamily" Molecules, 22:713 2017.
Rider et al. Heparin/heparan sulphate binding in the TGF-beta cytokine superfamily, Biochern Soc Trans, 34(Pt.3): 458-460 2006.
Villalvilla et al. "SDF-1 signalling: a promising target in rheumatoid disease" Expert Opinion on Therapeutic Targets; 18(9):1077-1087 2014.
Xu et al. "Association of CXCL12 levels in synovial fluid with the radiographic severity of knee osteoarthritis" J Invest Med, 60(6):890-901 2012.
Zhong et al "Development and preclinical characterization of a humanized antibody targeting CXCL12" Clin Cancer Res, 19(16):433-4445 2013.

\* cited by examiner

*** p≥0.001 vs

* p≥0.05 vs PLLA

Vertical scale marks=1mm

MEDICAL IMPLANT

STATEMENT OF PRIORITY

This application is a 35 U.S.C. § 371 national phase application of International Application Serial No. PCT/GB2016/052270, filed Jul. 25, 2016, which claims priority to GB Application No. 1513097.4, filed Jul. 24, 2015, the entire contents of each of which are incorporated by reference herein.

The present invention relates to an acellular, multi-layered medical device having bespoke, multifunctional bioactivity, for the purpose of regeneration of skeletal tissues. The invention includes inter alia uses of the medical device, especially but not exclusively, in promoting regeneration of articular cartilage in lesions of the joint surface and in promoting healing of joint tissues, for example, meniscal cartilage and tendon and ligament injuries and also healing of bone injury such as fractures or subchondral bone degeneration in joints. For completeness of understanding, this application includes inter alia preferred methods of fabrication of the medical device.

BACKGROUND

Biological/bioactive factors (BFs), including growth factors, differentiation factors, cytokines and chemokines are crucial in maintaining normal tissue homeostasis, and wound healing and tissue regeneration. This is also the case for the skeletal tissues including the cartilage covering the surface of the joint (articular cartilage), meniscal cartilage in the joint and tendons, ligaments and bone. Damage to skeletal tissues can be caused through trauma, for example, but not exclusively, torn ligaments and tendons and bone fractures. Damage to skeletal tissues can also be caused by degenerative diseases. One example is a degenerative arthritis such as osteoarthritis, which can particularly affect articular cartilage and subchondral bone. Osteoarthritis is the most common form of arthritis' causing painful joints, loss of mobility and significantly impaired quality of life[2,3] with an appreciable economic impact on health and social care costs of 1-2% GDP[4,5]. There is presently no cure for osteoarthritis and current surgical[6,7] and pharmacological therapies, whilst being able to give symptomatic relief, do not halt the joint degeneration[8-10]. Increasing numbers of younger adults (less than 65 years) are presenting to clinicians with advanced cartilage disease or post-traumatic osteoarthritis[11]. Traumatic injury of the joint tissues (articular cartilage, meniscal cartilage, bone, tendon and ligaments) is one risk factor for the subsequent development of OA[12]. Over 10,000 cartilage injuries warranting repair occur annually in the UK[13] and around 40% of traumatic cartilage lesions will lead to development of OA. Replacement of the osteoarthritic joints with prosthetic joints may ultimately be required to restore mobility. However, problems associated with joint prostheses include a finite working life[14] and may not provide the individual with the full range of natural movement as compared to a natural healthy joint. In addition, device loosening is a longer-term problem requiring invasive revision surgery[15] and is particularly problematic in younger more active patients (<60 years)[16-17], who tend to have an active lifestyle and so put more demands on their prostheses. Therefore, with an increasingly aging population, patients over 50 or 60 years of age may require at least one revisional surgery for knee prostheses.

An aging population and a need to prolong an individual's health and working capacity, coupled with the limitations of artificial joints, indicate a clinical requirement to prolong the functional pain-free life of joints to delay or prevent the need for joint replacement surgery. Currently there are four main approaches to regenerate the joint surface (articular) cartilage before the need for joint replacement. The first approach is the more common approach of using microfracture[6,7,18]. In this procedure, the surgeon trims the cartilage defect and drills down into the subchondral bone to release bone marrow cells to stimulate regeneration of new cartilage tissue. However, while giving valuable pain relief, a fibrocartilage tissue is formed which is biomechanically inferior to native hyaline cartilage and degenerates after several years. A second, more recent approach, is to place non-functionalised material implants into cartilage defects such as collagen matrices or sponges containing the substitute mineral hydroxyapatite to aid integration of the implant into bone. The third approach covers the developing cell therapy approaches, such as autologous chondrocyte implantation (ACI)[19-20] and matrix assisted autologous chondrocyte implantation (MACI)[21] which have shown promising results for regeneration of traumatic lesions of articular cartilage on an individual patient basis[22-24]. Both these cell therapies use autologous chondrocytes isolated from a cartilage biopsy and grown in the laboratory to obtain sufficient numbers for the procedure. Cells are either, placed into the defect area as a cell suspension and then held under a flap of periosteum or a collagen membrane (ACI), or they are embedded in a biomaterial scaffold then implanted (MACI). To date, patients treated with ACI or MACI are less than 50 years of age with cartilage lesions caused by trauma. However, these procedures require the patient to have two separate surgeries and currently, the cost of these technologies does not allow access to a wider patient population. Currently, neither ACI nor MACI are approved by the UK National Centre for Clinical Excellence (NICE)[13] so are not funded by the UK National Health Service, unless the patients are participant in a clinical trial investigating the efficacy of these procedures.

There is a clinical need for a cost-effective medical device to actively promote regeneration of the joint surface to delay or prevent joint replacement surgery. Regeneration of articular cartilage in situ requires the appropriate cell homing mechanisms, and retention of 'repair cells' [(e.g. mesenchymal stem cells (MSCs)] at the defect site. MSCs are present in the joint fluid (and in raised numbers in OA joint fluids[25]), and can be readily released from the bone marrow by surgical microfracture of the subchondral bone[8,18]. The stem cells must then undergo appropriate chondrogenic differentiation and synthesise a hyaline cartilage. It is well known that the extracellular matrix (ECM) of healthy articular cartilage, in common with the ECMs of other body tissues (such as bone), contains sequestered biological/bioactive factors (BFs) such as tissue growth factors, phenotype modulating factors and migratory factors for cell proliferation, differentiation and maintenance of chondrocyte phenotype and tissue integrity[6,26,27]. These BFs are tightly held within the extracellular matrix or at the cell surface with a large fraction of this potential bioactivity non-covalently bound through charge-charge interactions to sulphated glycosaminoglycan side chains (particularly heparan sulphate) of proteoglycans[28]. Most sulphated glycosaminoglycans (sGAGs) are present on the cell surface or in the extracellular matrix as extended O-linked side-chains of proteoglycans such as syndecans, perlecan and versican[29,30]. These sGAGs bind many biologically active molecules non-covalently through ionic interactions. These BFs can be mobilised when required through cell signalling[30], and/or proteinase action[55] or can act as concentration gradients of chemokines for cell migration[31]. Regarding the latter, the presence of sGAG-bound chemokines is thought to be crucial for the formation of chemokine gradients essential for migration and homing of stem cells[32]. The sequestering of bioactive molecules by sGAG moieties maintains their biological activity by sequestering them away from chemical and proteolytic degradation; moreover, sGAGs can enhance the interactions between the cell receptors and biological factor(s)[33-35]. Some BFs are unstable at body temperature (37° C.) or form oligomerised forms such as TGFβ3 and CXCL12 which are unstable in solution. Interaction of these factors with heparin is essential to induce the oligomerization and stabilisation of the molecular structures[36-38]. In addition, oligomerisation of some BFs is crucial for full biological function[39]. Hence, the co-presence of sGAGs and BFs and the resultant ionic binding interaction is important to protect and optimise the biological activity and interaction of many BFs with their target cell receptors and may be crucial for full activity in the body. In addition, sGAGs are often required for the interaction between biological factor and its cell receptor. These activities cannot be fully achieved by direct covalent attachment of bioactive factors to a surface.

Not all BFs found in extracellular matrices, such as native cartilage, bind directly to glycosaminoglycans; for example, the cartilage differentiating and matrix-stimulating factor MIA[40] is reported to bind to fibronectin. However, in these cases the bioactive factor may bind to a specific binding protein or an extracellular matrix protein which will bind to glycosaminoglycans. For example, fibronectin binds tightly to sGAG residues and also binds growth factors such as MIA[41]. Other examples of extracellular matrix proteins which have both growth factor and sGAG-binding sites are vitronectin and laminin[42,43].

The GAG sidechains of extracellular matrix proteoglycans are made up of repeating disaccharides with varying degrees of sulphation to form chondroitin sulphate, heparan sulphate, keratan sulphate and dermatan sulphate. It is known that these sulphated oligosaccharides and heparin (a mimic of the GAG, heparan sulphate) can directly bind many BFs, examples of which are bone morphogenic proteins, fibroblast growth factors and the transforming growth factor family of growth factors.

There have been reports of hydrogel and nanoparticle drug delivery systems containing heparin that has been chemically cross-linked to give covalently bound residues, followed by binding of single growth factors such as bone morphogenic protein-2 or fibroblast growth factor-2[44-47] or vascular endothelial growth factor[59]. This approach has been used to specifically and covalently bind heparin to a specified collagen scaffold using chemical a cross linker. The cross-linked, heparin-derivitised collagen scaffold was used to bind morphogenic protein-2[60]. However, this report does not show any biological activity of the bound BMP-2 nor any in vitro or in vivo biological activity nor covalent binding of other oligosaccharides or binding of any other BFs to the scaffold. Also, there are reports of various scaffolds which have been soaked in a single growth factor to enable physical absorption to the scaffold surface, or growth factors have been directly bound to a surface or scaffold through a chemically-induced covalent binding or use of streptavidin-labelled growth factors bound to biotin-labelled scaffolds or physical entrapment.

Ionic binding interactions are essential for intercellular, extracellular and intracellular biological reactions needed for life. Such interactions include but are not exclusive to protein-protein interactions and protein-ligand interactions (such as binding of bioactive factors to their target cell receptors and cell signalling), nucleotide-protein interactions and carbohydrate-protein interactions (such as sequestering of bioactive factors by extracellular matrices). Hence, ionic interactions are essential to biochemical, chemical, biomaterial and cell biology methodologies to enable biological mimicry. Ionic interactions are also essential for modification of surfaces to build up alternative layers of anionic and cationic charges, for example layer-by-layer technologies which are well described in the scientific literature[47]. This approach has been used to bind a protein antibody to the biological factor TGFβ2[54] to the surface of an artificial lens. It should be noted that this report described the binding of an antibody and not binding of the active biological factor TGFβ2 to the artificial lens surface nor described binding of sulphated oligosaccharides or other sulphated moieties. As predicted by their high negative charge, sulphated glycosaminoglycan moieties (sGAGs) will bind tightly to positively charged surfaces such as those modified with amine groups deposited, for example, by covalent binding, layer-by-layer technologies[47] or plasma deposition[48-50]. Therefore, positively charged surfaces such as amine-modified surfaces can be used to immobilise glycosaminoglycans and oligosaccharides derived therefrom[51]. Binding of sGAGs through ionic interaction ensures that they are permitted to assume a conformation to enable interaction with BFs and cell receptors. Therefore, heparin-binding can be sequestered to the immobilised glycosaminoglycan oligosaccharides in a form that can be utilised by cells and tissues. Use of just an anionic surface to bind bioactive factors such as chemokines and growth factors, does not permit the co-presence and co-activity of sGAGs and bioactive factors which is an important feature to protect and optimise the biological activity and interaction of many bioactive factors with the target cell receptors and may be crucial for full activity in the body First reported in 2004[50], positively charged amine-functionalised glass and plastic surfaces can bind sGAGs through ionic interaction. Heparin bound to the amine-functionalised surfaces of multi-well assay plates has been shown to bind single, known heparin-binding growth factors BMP2[52], osteoprotogerin, TSG6 and TIMP3[53] However, these publications did not show biological activity of the bound ligands nor biocompatibility of the functionalised surfaces, nor binding of these biological factors to polymer scaffolds. More recently the same research group (WO 2014/153610)[51] described immobilisation of heparin to an amine functionalised cell culture plate and a scaffold of polycaprolactone. The binding of fibroblast growth factor 2 (FGF-2) and platelet-derived growth factor (PDGF), was shown[51]. for the purpose of using the growth factor immobilisation for in vitro cell culture of epithelial cells, dermal fibroblasts, keratinocytes and retinal pigment epithelial cells and tissue engineering of skin substitutes for wound repair and laboratory skin models. However, WO 2014/153610[51] does not report any studies to provide evidence for in vivo activity.

There remains a need for a cell-free medical device for regeneration of skeletal tissues e.g. articular cartilage, meniscus, ligaments and tendons or bone. The invention described hereinafter provides a medical device containing combinations of several bioactive factors to promote in vivo cell homing of mesenchymal stem cells to a cell-free medical device and also promote appropriate cell differentiation and tissue formation. These combinations of bioactive factors can be customised to promote regeneration of articular cartilage, meniscal cartilage, ligaments and tendons or bone.

BRIEF SUMMARY OF THE DISCLOSURE

The invention is an acellular, multifunctional, biomimetic medical device designed to be used as a medical implant which, depending on its selected bioactive factors, can be used to regenerate articular cartilage, bone, meniscal cartilage, and ligament or tendon tissues in the body. The novelty lies in the custom application of more than one biological factor, each bound to GAG oligosaccharides in a biomimetic way, at low levels (nanogram/picomole amounts) to a known scaffold material. These factors can be chosen to stimulate stem cell homing into the implant and stimulate appropriate differentiation to the required cell type and promote tissue formation. In addition the sulphated oligosaccharides are also required for full biological activity and interaction of biological molecules with the target cell. Hence, by customisation of the bioactive factors and scaffold material, the device can designed to be used as a medical device to promote regeneration of articular cartilage, bone, meniscal cartilage, and ligament or tendon tissues in the body.

The medical device of the invention contains multiple bioactivities stored at novel low levels (nanogram/picomole) in a biomimetic manner to optimise the regenerative capacity. The medical device can be customised to actively promote both homing of stem cells into the device and promote their differentiation into the required cell type to produce de-novo tissue formation.

According to a first aspect of the invention there is provided a biomimetic medical device comprising a scaffold coated in or adsorbed on its surfaces a first layer comprising a cationic agent, the first layer being covered or coated with a second layer comprising an anionic polysulphated moiety, which is non-covalently bound to at least one or more biological/bioactive factors selected from the groups comprising:
 (i) an agent that can stimulate stem cell differentiation and/or promote appropriate extracellular matrix formation for the tissue to be regenerated;
 (ii) an agent that inhibits enzymes associated with the break down or catabolism of extracellular matrix; and
 (iii) a stem cell homing or migratory factor.

According to a first aspect of the invention there is provided a biomimetic medical device comprising a scaffold coated in or adsorbed on its surfaces a first layer comprising a cationic agent, the first layer being covered or coated with a second layer comprising an anionic polysulphated moiety, which is non-covalently bound to at least one or more bioactive factors selected from the groups comprising:

The device of the present invention is fabricated as a multi-layered appliance, comprising a scaffold core surrounded by a first layer, the first layer comprising a cationic material surrounded by a second layer comprising an anionic layer such as a polysulphated oligosaccharide and a third layer comprising of at least one bioactive factor. In this configuration the medical device of the present invention provides a biomimetic, biofunctional medical device implant.

Preferably, said first and second layers are non-covalently bound together.

Preferably, the scaffold is synthetic or natural and is selected from the group comprising polyester compositions such as polylactic acid, poly(lactic-co glycolic acid) compositions, polycaprolactone, polyester-polyallylamine copolymers, collagen, peptide-based/modified scaffold materials, silk, chitosan-based polymers, hyaluronan-based polymers, decellularised tissue, tri-calcium phosphate, hydroxyapatite, and ceramic based biomaterials and combinations and compositions of the foregoing scaffold materials with tricalcium phosphate, hydroxyapatite or ceramic based biomaterials.

In a preferred embodiment of the invention the scaffold is a non-woven, porous scaffold such as an electrospun biomaterial such as poly-L-lactic acid, or co-polymers of poly-L-lactic acid and poly-L-glycolic acid, or polycaprolactone manufactured to enable fibre size, degree of cross linking, diameter and orientation to be controlled and tailored to the tissue to be regenerated.

Preferably, the first layer comprising the cationic agent is a stable unsaturated amine, more preferably it is allylamine.

Preferably, the second layer contains an anionic oligosaccharide layer selected from the group comprising heparin and oligosaccharides derived from heparin, heparan sulphate, dermatan sulphate, chondroitin-4-sulphate, chondroitin-6-sulphate, hyaluronic acid, hyaluronan, keratan sulphate and pentosan polysulphate.

Preferably, one or more bioactive factor(s) is non-covalently bound to the anionic material either directly or indirectly. In the instance that the bioactive factor(s) is bound indirectly to the polysulphated moiety it is bound via a linker moiety. An example of a linker moiety is one which binds to the anionic layer whilst the bioactive factor does not bind directly to the anionic layer but will bind to the linker moiety. A particularly effective linker moiety is fibronectin and its peptide derivatives. Other examples are insulin-growth factor binding protein, vitronectin and laminin and their peptide derivatives.

Preferably the bioactive factor(s) is selected from the group comprising transforming growth factor β group such as TGFβ1 and TGFβ3 and including the bone morphogenetic proteins (BMPs), connective tissue growth factor (CCN2), fibroblast growth factor family, heparin binding EGF-like growth factor, fibronectin and fibronectin fragments, melanoma inhibitory activity, insulin-like growth factor bound to IGF binding protein, platelet derived growth factors, vascular endothelial growth factors, heparin-binding chemokines including but not restricted to CXCL12, SDF1β, CCL2 (MCP-1), CCL21, CXCL1, CXCL8 (IL-8), tissue inhibitor of metalloproteinase-3, osteoprotegerin, Wnt proteins such as Wnt 3a, DNA complexes and DNA plasmid/viral complexes polycationic vesicles or complexes of RNA including microRNA and derivatives or biologically active fragments of all aforementioned factors.

Preferably, the medical device includes a mixture of a plurality of bioactive factors. In some embodiments of the invention the implant may also include further modification of the bioactive implants in order to enhance implant fixation by for example, deposition of hydroxyapatite particles by an alternative soaking method[62], into one end to create an 'osseous' region to promote early incorporation of this region with the subchondral bone. This osseous region) could also be surface modified with a cationic agent such as allylamine as described herewithin, followed by binding of an anionic agent such as a polysulphated moiety to which appropriate bioactive factors could be bound to promote bone regeneration such as, but not exclusively, Wnt 3a or BMP2. Alternatively, the device may be composed of two different scaffolds to form an osteochondral scaffold. Both the chondral and osseus portions may be functionalised with appropriate bioactive factors to promote cartilage and bone regeneration respectively. Accordingly the implant may comprise several different bioactive factors in different regions of the same device.

According to a further aspect of the invention there is provided a method of constructing the medical device of the first aspect of the invention comprising:

(i) providing a scaffold core;
(ii) coating the scaffold surfaces or impregnating the scaffold surfaces with a first layer of a cationic material;
(iii) covering the first layer of cationic material with a second layer of an anionic oligosaccharide or polysulphated moiety; and
(iv) attaching at least one bioactive factor non-covalently either directly to said second layer or indirectly via a linker moiety to said second layer.

Preferably, in the instance that the scaffold is comprised of polylactic acid or its copolymers (for example, polylactic acid-polyglycolic copolymers) or polycaprolactone, it is electrospun.

Preferably, the surface of the scaffold is coated or covered with the first layer material by plasma polymerisation.

According to a further aspect of the invention there is provided use of the biomimetic medical device of the first aspect of the invention as an implant for the promotion of healing of lesions in a joint surface caused for example by trauma or early osteoarthritis and promoting healing of meniscal cartilage, bone, tendon and ligament injuries or tissue degeneration.

According to a yet further aspect of the invention there is provided a method of promoting mesenchymal stem cell differentiation into chondrocytes or promoting cartilage extracellular matrix formation, the method comprising implanting the device of the first aspect of the invention into an area of a joint or other area to be treated.

Preferably the joint is a synovial joint. Synovial joints are a naturally rich source of mesenchymal stem cells which are found in the joint fluid, synovial lining, cartilage and bone marrow. It is envisaged the medical device could be implanted into a cartilage defect in combination with surgical microfracture (a common orthopedic procedure) or with addition of non-cultured, minimally manipulated bone marrow which could be extracted by bone biopsy during implantation of the medical device and added to the joint fluid during the implantation procedure. It is envisaged that the bioactive factors of the present invention on the outer surfaces of the device can be used to actively promote stem cell homing into the implant and encourage differentiation in situ.

According to a yet further aspect of the invention there is provided a method of incorporating agents for example but not exclusively, Tissue Inhibitor of Metalloproteinases (TIMP) to inhibit enzymes associated with the breakdown or catabolism of extracellular matrix or the cartilage matrix comprising implanting the device of the first aspect of the invention into an area of a joint or other area to be treated.

According to a yet further aspect of the invention there is provided a method of encouraging stem cell homing comprising implanting the device of the first aspect of the invention into an area of a joint or other area to be treated.

According to a yet further aspect of the invention there is provided a method of treating or promoting healing of lesions in a joint surface or subchondral bone caused for example by trauma, or an early osteoarthritis, or promoting healing of meniscal cartilage, tendon and ligament injuries and bone fracture comprising implanting the biomimetic medical device of the first aspect of the invention into an affected area of a patient.

According to yet another aspect of the invention, the device may be constructed of a chondral portion attached to, or modified with an osseous region, to form an osteochondral device to aid implant fixation in the joint surface and underlying subchondral bone. Such a device may be fabricated, for example, by: 1). deposition of hydroxyapatite onto a portion of a chondral scaffold or by 2). electrospinning a chondral portion onto a bone substitute material such as hydroxyapatite, or by 3). physical attachment of the chondral medical device to a bone substitute material using for example but not exclusively, heat annealing or fibrin sealants).

It will be appreciated that all features ascribed to one aspect of the invention apply mutatis mutandis to each and every aspect of the invention.

BRIEF DESCRIPTION OF THE DRAWINGS

Embodiments of the invention are further described hereinafter with reference to the accompanying drawings, in which:

FIG. 5 also shows an example of a biological factor (MIA) (FIG. 5F) binding to a specific binding protein or an extracellular matrix protein (fibronectin) which will bind to glycosaminoglycans. Results are the means+/−standard error of the mean.

FIG. 6 are scanning electron micrographs of bovine synovial fluid mesenchymal stem cells 48 hr after seeding the cells onto PLLA (FIG. 6A), and PLLA scaffolds functionalised with allylamine (FIG. 6B), heparin (FIG. 6C) and TGFβ3 (FIG. 6D). Scale bars on the micrographs=50 μm.

FIG. 7 are scanning electron micrographs of the chondrocytes 48 hr after seeding the cells onto PLLA (FIG. 7A), and functionalised PLLA scaffolds: allylamine (FIG. 7B), heparin (FIG. 7C) and TGFβ3 (FIG. 7D). Scale bars on the micrographs=100 μm.

FIG. 8A shows the cell viability of human bone-marrow mesenchymal stem cells cultured on control (PLLA) and examples of functionalised scaffolds 48 hr after seeding the scaffolds with the cells. The cells were cultured in basal medium in the absence of serum or additional growth factors. Results are the mean+/−standard error of the mean (SEM). FIG. 8B shows the viability of synovial fluid-derived mesenchymal stem cells cultured on control (PLLA) and examples of functionalised scaffolds after seeding the cells onto the scaffolds. The cells were cultured in basal medium in the absence of serum or additional growth factors. Results are the mean+/−SEM. FIG. 8C shows the cell viability of bovine articular chondrocytes cultured on control (PLLA) scaffolds and example functionalised scaffolds 48 h after seeding the scaffolds with the cells. The cells were cultured in basal medium in the absence of serum or additional growth factors. Results are the mean+/−SEM. FIG. 8D shows the viability of human bone marrow-derived stem cells cultured on control (PLLA) and examples of the functionalised scaffolds 72 hr after seeding the scaffolds with the cells. The cells were cultured in basal medium or osteogenic medium in the absence of serum or additional growth factors. Results are the mean+/−SEM. FIG. 8E shows the viability of human osteoblastic cells on examples of the functionalised scaffolds 48 hr after seeding the scaffolds with the cells. The cells were cultured in basal medium in the absence of serum or additional growth factors. Results are the mean+/−SEM.

FIG. 10A shows the results for individual experimental scaffolds and the group means of the extracellular GAG accumulation in the absence of added serum or growth factors at 33 days. FIG. 10B shows the extracellular GAG accumulation in the absence of added serum or growth factors at 44 days. Results show the mean+/−SEM.

FIG. 11 shows the rate of glycosaminoglycan (GAG) accumulation in the culture medium which is a measure of proteoglycan synthesis indicative of chondrogenic differentiation of the mesenchymal stem cells.

FIG. 13 shows immunolocalisation of collagen II in constructs formed from bovine articular chondrocytes cultured on PLLA or functionalised scaffolds of PLLA for 35 days in basal medium in the absence of serum or additional growth factors. All images were taken at magnification of ×20. Scale bars=100 μm.

FIG. 15 shows the gross appearance of example tissues retrieved at post-mortum 28 days after surgery.

FIG. 16A is a diagram (not to scale) showing the basic components of an osteochondral implant. In this device, the chondral portion would be composed of a biological factor-functionalised scaffold as described herewithin. The osseous part could be formed by deposition of hydroxyapatite or brushite onto one end of an electrospun scaffold or by heat annealing or using a biological adhesive (for example, fibrin sealant) to attach an osseous scaffold onto a chondral portion. Alternatively, a chondral portion could be directly electrospun onto an osseous scaffold. This latter design is exemplified in FIGS. 16B and 16C which show photographs of an osteochondral medical device comprised of a hydroxyapatite disc osseous region onto which was electrospun a 1.8 mm random-fibre scaffold of polycaprolactone (PCL) to form the chondral portion. After fabrication the scaffold portions could be functionalised with bioactive factors as described herewithin. FIGS. 16D, 16E and 16F are scanning electron micrographs of the PCL chondral portion which was directly electrospun (depth 1.8 mm) onto the osseous scaffold (1 cm ceramic disc) of hydroxyapatite.

DETAILED DESCRIPTION

Figure 1:
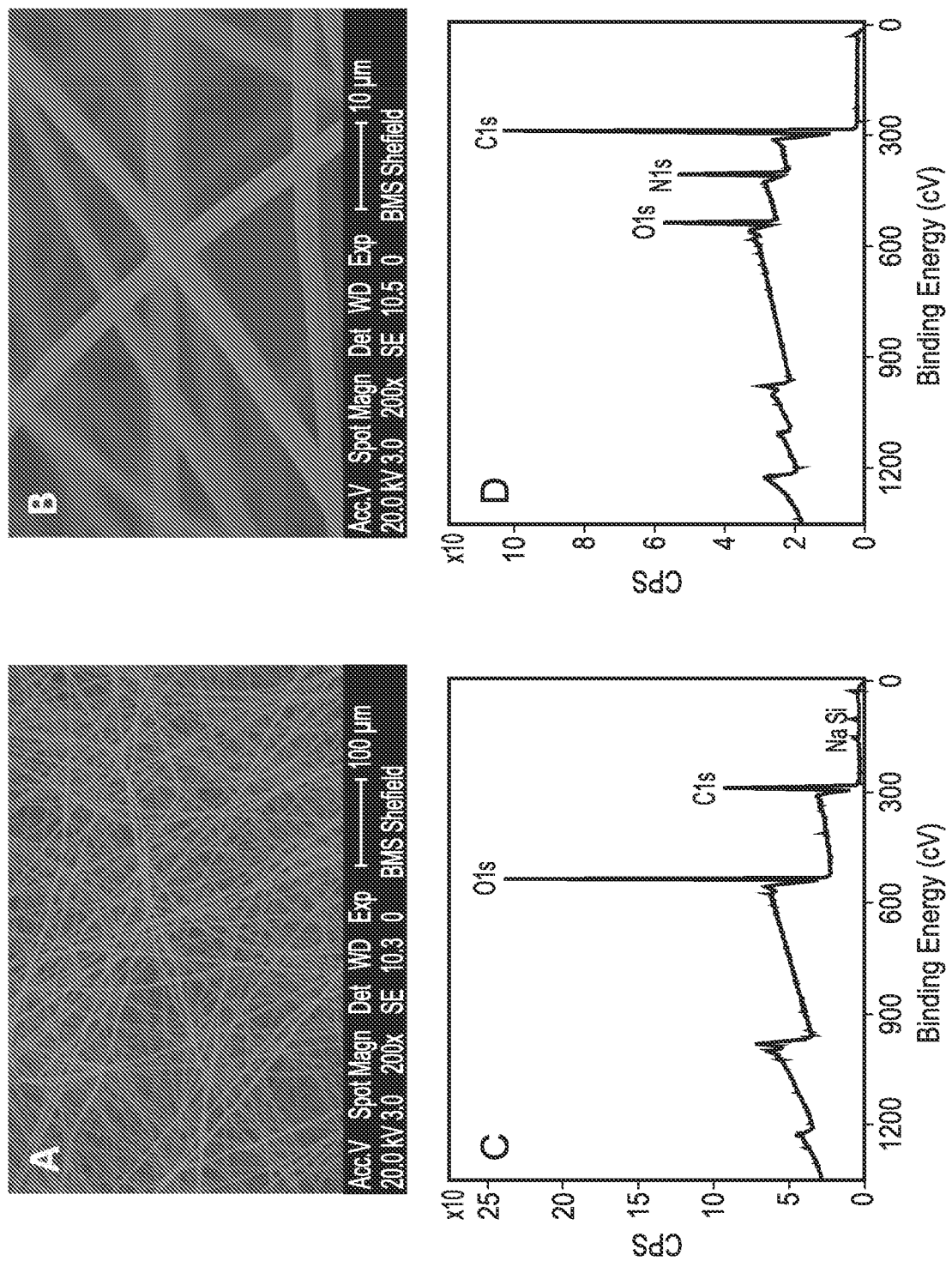
FIGS. 1A and 1B are scanning electron microscope images of the electrospun PLLA. Scale bar in 1A=100 μm. Scale bar in 1B=10 μm.
FIGS. 1C and 1D are X-ray photon spectroscopy images of the PLLA scaffolds before (1C) and after (1D) cold plasma treatment with allylamine using the described methods.

Reference herein to a "scaffold" is intended to include a three dimensional structure that provides a matrix onto which the first, second and biological factor can be layered.

Reference herein to "biomimetic" is the imitation of models, systems, and elements of nature for the purpose of solving complex problems associated with tissue repair and promotion of tissue healing.

The terms "surfaces" and "surface" of a scaffold are interchangeable. Scaffolds comprise many surfaces (rather than just a top, bottom and sides) as they have many internal surfaces such as internal fibres and pores-which would be coated by the methodology of the present invention. The term surfaces include internal and external surfaces of the scaffold.

Reference herein to "layer" is intended to include a coating, covering, film or an additional and different surface to the base surface onto which it is applied.

Healthy ECM of tissues such as, articular cartilage contains stored biological/bioactive factors (BFs), which maintain the health and phenotype of the cells within the tissue and tissue integrity. These BFs are sequestered by their tight non-covalent binding to matrix sugar-based moieties [glycosaminoglycans (sGAG)] of ECM cartilage proteoglycans. This sequestration also prevents the BFs from rapidly leaching from the cartilage and protects them from degradation by proteolytic enzymes. Heparan sulphate GAGs are involved in BF-cell interactions, maintaining the BFs where they are required by the cells, thus reducing the concentration of BFs needed for biological activation. Therefore, the incorporation of growth factor-binding sGAG surfaces could be extremely useful in the generation of biofunctional, biomaterial implants that can present bioactive molecules such as growth factors in a structural and biochemical context using the same mechanisms as those found in native musculoskeletal tissues (for example, articular cartilage)

The present invention is not directed towards tissue engineering of de novo tissues for subsequent implantation but rather the invention is a cell-free, multi-layered medical device having multifunctional bioactivity directed towards regeneration of joint tissues for subsequent use in vivo.

The implants of the present invention mimic the natural biological factor(s)-sequestering mechanism in the ECM of tissues, for example cartilage, so that selected chondrogenic and stem cell migratory factors can be bound in the implant in a similar structural and biochemical context as found in native cartilage. Also low physiological concentrations of the BFs are required so reducing both cost and potential side-effects. Further modification of the bioactive implants can be made by deposition of hydroxyapatite particles into one end to create an 'osseous' region to aid implant fixation by promoting early incorporation of this region with the subchondral bone. This technology permits fabrication of an 'off-the-shelf', innovative medical device with several bioactivities incorporated to both promote migration of repair cells (stem cells) and maturation of the stem cells into cartilage cells and so promote tissue regeneration at the site of injury. In addition, the technology is adaptable to allow fabrication of sophisticated biomimetic scaffolds containing differing BFs to optimise cartilage regeneration in cell therapy approaches to cartilage repair such as matrix-assisted chondrocyte implantation.

A particular advantage of the device of the present invention is that, since the BFs are bound non-covalently in a potentially reversible manner, it allows for the possibility of conformational change to release in the vicinity of cells, and to allow optimal interaction with cell-surface receptors.

Preparation of Poly-L-Lactic Acid and Poly-Caprolactone Scaffolds by Electrospinning A solution of poly-L-lactic acid (PLLA) or poly-caprolactone (PCL, Sigma) was prepared at 12% (w/v) in dichloromethane The polymer solution was placed in a 1 ml glass syringe fitted with a 2.5 cm 20-G needle (Fisnar). An 18 kV electric field was applied at a distance of 20 cm between an aluminium foil sheet covering a flat metal plate and the needle tip to form an electrospun PLLA mat composed of randomly oriented, 5 µm microfibres on the aluminium foil. Alternatively, solutions of PLLA or PCL, were prepared in glass syringes as above and 18 kV was applied at 20 cm between needle and a rotating foil sheet collector. An electrospun mat was collected composed of randomly oriented microfibres with a diameter of 5 µm and mat thickness of 1.8 mm. The electrospun mats were left overnight to allow the volatile solvent residues to escape. Heat annealing the microfibers was performed by heating the PLLA scaffolds at a melting temperature of 173° C. and heating PCL scaffolds at a melting temperature of 60° C.

Preparation of Osteochondral Scaffolds

PLLA and PCL fibres were also electrospun directly on to hydroxyapatite porous disks using the same processing parameters as above, to a 1.8 mm thickness. PLLA scaffolds were heat annealed onto the hydroxyapatite porous disks at a melting temperature of 173° C. PCL scaffolds were heat annealed on the hydroxyapatite porous disks at a melting temperature of 60° C.

Scanning Electron Microscopy of Electrospun Matrices

The architecture of the electrospun matrices was analysed by scanning electron microscopy (SEM Philips XL-20) at an accelerate voltage of 10 kV. Before SEM analysis, samples were coated with gold using a sputter coater. The SEM magnification (6000×) was selected to have a squared analysis field of 50 µm. The fibre diameters and distribution were quantified by analysing the SEM micrographs using ImageJ software. Three images of three different zones of three samples were analysed and the pore and fibre diameters were determined.

Plasma Polymerisation

Allylamine (Sigma Aldrich ≥99%) plasma polymerisation was conducted in a stainless steel vacuum reactor chamber. The flow of allylamine vapour into the chamber was adjusted using manual needle valves. The reactor was evacuated to less than $2 \times 10^{-3}$ mbar, using a vacuum pump. A liquid $N_2$ cold alumina trap was used to protect the pump from monomers and their escape via the exhaust. The allylamine monomer was degassed using 3 freeze-thaw cycles. The plasma was ignited using a radio frequency generator at 13.56 MHz and the treatment was performed at a power of 10 W and a flow rate of ~2 standard unit cm/min (sccm) for 20 min.

Heparin Coating of Scaffolds

For the preparation of heparin-functionalized scaffolds (PLLA-pAAm-HP), the allylamine-treated (pAAm) PLLA electrospun scaffold (200 µm) was cut into circular discs with diameters of 5-6 mm. These were placed individually in wells of a 96 well culture plate, sterilized with 200 µl of 2-Propanol (isopropanol) at ambient temperature for 15 minutes and, after 3 washes with PBS, incubated overnight in the dark at ambient temperature with 200 µl of 50 µg/ml heparin (Iduron, low molecular weight, porcine mucosa) solution in PBS. Unbound heparin was removed by washing 3 times with PBS.

X-Ray Photon Spectroscopy

PLLA, PLLA-pAAm and PLLA-pAAm-Hp scaffolds were analysed by X-ray photoelectron spectroscopy analysis (XPS) (K-alpha, Thermo Scientific). Amine derivate deposition on PLLA-pAAm membranes was checked by measuring the C1s and N1s signals, while the adsorption of the heparin on the PLLA-pAAm-Hp membrane was detected using the sulphur signal S2p.

Quantitative Assessment of Bound Heparin

[$^3$H]-heparin (Hartmann, low molecular weight, 1 mCi/mg, 1 mg/ml) was diluted 1/10 with cold heparin (Iduron) to give 1 mg/ml heparin, 100 µCi/mg. PLLA-coated scaffolds were placed in minifuge tubes. The 1/10 hot/cold heparin stock solution was aliquoted onto the scaffolds to give final amounts of 0-70 µg in 10 µg (0.01 µCi) increments (2 replicates/dose) in 1 ml final volume of PBS. The tubes were gently vortexed then left overnight at 4° C. The next day the tubes were briefly centrifuged, the supernatant was poured off, 1 ml of PBS was added, the tubes were gently vortexed and kept at 4° C. for 20 min, before centrifugation and removal of supernatant. This washing step was repeated twice more. 100 µl of 5M NaCl was added to each tube to dissociate the bound heparin from the scaffold. After 20 min at 4° C. the tubes were briefly centrifuged. The supernatants were dispensed into scintillation vials and replaced with another 100 µl of 5M NaCl. After 60 min at 4° C. the tubes were centrifuged again and the supernatant was dispensed into the same scintillation vial. This was replaced with a third 100 µl 5M NaCl which was left at 4° C. overnight. The following day the tubes were again centrifuged and the supernatant was added to the ones already present in the scintillation vial. 2 ml of scintillant (Ultima Gold) was added to the tubes which were placed in the scintillation counter (Beckman LS6500) and counted for 2 minutes. Disintegrations per minute (dpm) were provided automatically and converted to µCi from which the amount of bound heparin (µg) was calculated.

Quantitative Assessment of the Binding of Bioactive Factors to Sulphated Oligosaccharides.

Oligosaccharides were incubated for 18 h at ambient temperature with allylamine-functionalised 96-well plates. Each well contained 10 ng of oligosaccharide in 200 µl of PBS. After incubation, the wells were drained and washed 3 times with PBS. 300 µl of PBS containing 5 mg/ml ELISA grade BSA (Sigma) was added/well and the plates incubated for 1 h at ambient temperature to block non-specific protein binding to the well surfaces. The plates were then drained of their contents and the wells washed 3 times with PBS/0.05% Tween 20. Bioactive factors were diluted in PBS containing 1 mg/ml BSA and 200 µl added per well (10 ng/well TGFβ1 or TGFβ3, 25 ng/well CXCL12 or SDF1β, 50 ng/well MIA, 20 ng/ml Wnt 3a, or 20 ng/ml BMP2) The plates were incubated with the bioactive factors for 5 h at ambient temperature after which the growth factors were removed and the plates washed with 3 changes of PBS/0.05% Tween 20. Specific rabbit polyclonal antibodies for each biological factor (PreproTech), were added at appropriate dilutions in PBS/BSA (200 µl/well) and the plates were incubated overnight at 4° C. After incubation, the plates were drained, washed three times with PBS/0.05% Tween 20 and 200 µl of a goat-anti-rabbit alkaline-phosphatase-labelled antibody in PBS/1 mg/ml BSA was added/well and incubated for 1 h at ambient temperature. The plates were then washed three times in PBS/0.05% Tween 20 followed by addition of 1 mM p-nitrophenol phosphate in a 100 mM glycine-NaOH buffer pH 9.4 containing 1 mM MgCl$_2$. The rate of cleavage of the p-nitrophenol was followed spectrophotometrically at 405 nm using a TECAN Infinite M200 plate reader. For binding experiments where MIA was added to fibronectin-bound wells. The methodology was carried out as described above except that after blocking the plates with PBS/BSA and washing the wells with PBS, 250 ng/well of human fibronectin (R&D Systems) in PBS containing 1 mg/ml BSA was added. The plates were incubated for 3 h at ambient temperature and then unbound fibronectin removed by aspiration and draining the plates on paper towel. 50 ng well of MIA was then added and the assay completed as described above for the other BFs.

Coating of Oligosaccharide-Functionalised Scaffolds with Bioactive Factors

Oligosaccharide-functionalised scaffolds (5-6 mm) were incubated with 200 µl of PBS containing 1 mg/ml bovine serum albumin (BSA) containing the required concentrations of bioactive factors, for example TGFβ and CXCL12 (PeproTech) and incubated for 4-5 h (ambient temperature) or 18 h (4° C.). Scaffolds were then washed three times with PBS containing 1 mg/ml BSA.

In Vitro Cell Seeding of Scaffolds

Bovine synovial fluid mesenchymal stem cells (SF-MSCs) and articular chondrocytes (BAC) were isolated and monolayer cultures established as described previously[54,25]. Human bone marrow-derived mesenchymal stem cells (hBM-MSCs) were purchased from Promocell and monolayer cultures established as described for SF-MSCs. Cell culture reagents were purchased from Sigma or Promocell. Cells were removed from the culture dishes by trypsinisation, pelleted by centrifuging at 190×g for 5 min and then re-suspended in medium [Chondrocytes: Dulbecco's Modified Eagle's Medium (4,500 mg/l glucose), containing 10 mM HEPES buffer pH 7.4, 100 units/ml penicillin/100 µg/ml streptomycin, MEM nonessential amino acids, and 5% (v/v) foetal calf serum. MSCs: Dulbecco's Modified Eagle's Medium (1,000 mg/l glucose), 100 units/ml penicillin/100 µg/ml streptomycin, MEM nonessential amino acids, and 5% (v/v) MSC qualified foetal calf serum].

Sterile 5-6 mm diameter scaffolds were placed individually into wells of 24-well plates (suspension culture grade). $5×10^5$-$1×10^6$ cells were added per scaffold in a total volume of 1 ml of culture medium and incubated for 24-48 h at 37° C. on an orbital shaker (75 rpm). The chondrocytes/scaffold constructs were transferred to 12 wells (1 construct/well) and cultured in the above DMEM containing 1 mg/ml BSA, ITS (10 µg/ml insulin, 5.5 µg/ml transferrin, 0.5 µg/ml selenium and 4.7 µg/ml each of linoleic and oleic acids) and 25 µg/ml L-ascorbic acid (plus $10^{-7}$M dexamethasone for MSCs). The constructs were cultured at 37° C. on an orbital shaker (30 rpm) for the required time with replacement of the culture medium every 3-4 days.

Assessment of Cell Viability

Prestoblue® assay: Cell activity of the cell/scaffold constructs was determined by measuring the rate of conversion of resazurin dye to the fluorescent resorufin using the commercial resazurin dye preparation Prestoblue®. The assay was performed according to the manufacturer's instructions and resorufin formation followed by determining fluorescence with a plate reader (TECAN Infinite M200) with an excitation wavelength of 535 nm and emission wavelength of 590 nm.

Scanning Electron Microscopy

Constructs were washed with PBS and fixed with 3% (v/v) glutaraldehyde. Fixation was performed at 4° C. for 45 minutes. Samples were washed twice in 100 mM cacodylate buffer, pH 7.4, for 10 min at ambient temperature. The constructs were washed with PBS, and 1% (w/v) osmium tetroxide, buffered in 100 mM cacodylate, pH 7.4, was added for 1 h. Finally, the samples were dehydrated by exposure to increasing concentrations of ethanol (from 10% to 100%) and then left to air dry. The samples were gold-coated using a sputter coater at 15 mA for 1.5 min. Coated samples were then examined by scanning electron microscopy (SEM) (Philips XL-20).

Histology of Cell/Scaffold Constructs

At the end of culture, the constructs were blotted with tissue, weighed and either frozen at −20° C. for biochemical analyses or mounted in cryoprotectant (OCT compound, BDH, Gurr®) and 8-μm frozen sections were cut and fixed for 30 min at 4° C. in 4% paraformaldehyde (Sigma P-6148) solution in PBS. The tissue sections were washed twice in distilled water, air-dried overnight and stored at 4° C. until they were used for staining procedures.

Collagen II localisation: Immunolocalisation of type II collagen was performed in fixed sections. Sections were washed in PBS and pre-treated with 10 mg/ml hyaluronidase (Sigma H-3506) in PBS for 30 minutes at 37° C. followed by 2 mg/ml pronase (Sigma P-5147), for 30 minutes, at 37° C. The sections were washed in PBS and endogenous peroxidase activity was quenched with 3% hydrogen peroxide in 50% methanol (BDH 101586 6B) for 5 minutes. Sections were washed in Tris-buffered saline (TBS) solution and blocked with 3% BSA (Sigma A-2153) in TBS/Tween 20 (Sigma Ultra P-7949) for 1 hour to avoid non-specific staining. Sections were then incubated with primary antibody goat anti-type II collagen UNLB 1320-01 (Southern Biotech) overnight at 4° C. The next day, sections were washed once with high salt wash solution and twice in TBS/Tween 20, 10 minutes each and then incubated with biotinylated anti-goat IgG for 1 hour at room temperature. The tissue sections were washed with PBS and incubated for 30 min with ABC reagent from the Vectastain Elite ABC Kit PK-6105 (Vector Laboratories Ltd, UK) according to the manufacturer's instructions. Diaminobenzidine tetrahydrochloride (DAB, Vector DAB Kit, Vector Laboratories Ltd, UK) was prepared according to the manufacturer's instructions and incubated with the tissue sections for 2-10 min until a brown colour developed.

Quantitation of Extracellular Matrix in Cell/Scaffold Constructs

Proteoglycan content of the constructs was assessed by measuring the glycosaminoglycan (GAG) content[61]. Constructs were digested overnight at 60° C. in a papain digestion buffer [0.05% papain (from papaya latex), 6 mM n-acetyl cysteine in 200 mM phosphate buffer pH 6.8 containing 1 mM EDTA]. After digestion, scaffold fragments were pelleted by centrifugation (7,450×g for 10 minutes) and the GAG concentration of the supernatants was analysed using 1,9-dimethylmethylene blue (DMB, Sigma 341088). 50 μl of sample was then mixed with 250 μl of DMB solution (0.0016% DMB in 40 mM glycine-HCL buffer pH 3.0 containing 40 mM NaCl) and the optical density measured at 525 nm using a TECAN infinite M200.

In Vivo Sheep Study

An in vivo proof of concept study of the biomimetic implant design was carried out using a sheep model of a surgically—created, 6 mm diameter, full cartilage defect (2 mm) in the medial, femoral condyle articular cartilage of the knee. The sheep model is the most appropriate robust, weight-bearing model for assessing efficacy of medical devices and is used for pre-clinical confidence in concept before translation into man. Twenty four ewes (Mules, weight 58-73 kg, 2-3 years of age) were randomly allocated into three treatment groups: 1) control group which had a surgical defect only, no implant insertion, 2) surgical defect treated with control implant (heparin only-functionalised), or surgical defects with the active implant inserted (TGFβ3 and CXCL12-functionalised implant). A 1.8 mm thick electrospun PLLA scaffold was prepared from clinical grade PLLA under clean room conditions (Electrospinning Company). The scaffold was then surface modified by cold plasma treatment with allylamine. Prior to each surgery, 6 mm diameter scaffolds were sterilised with isopropanol, washed three times with PBS and incubated overnight at ambient temperature with 100 μg/ml low molecular weight heparin (Iduron). The scaffolds were then washed three times with PBS. For control implants, the heparin—functionalised scaffolds were incubated overnight at 4° C. in PBS/0.1% ovine serum album (OSA, Sigma). The active implants were prepared by incubating the heparin—functionalised scaffolds overnight at 4° C. with TGFβ3 and CXCL12 [100 μg/ml (PreproTech) in PBS/0.1% OSA]. The scaffolds were then washed in PBS/0.1% OSA, drained and kept on ice. The implants were warmed to ambient temperature before insertion into the cartilage defects. 6 mm defects were surgically created in the centrodistal region of the medial femoral condyle of anaesthetised animals using a 6 mm biopsy punch and scalpel to remove articular cartilage down to the subchondral bone. A full thickness cartilage defect was created and the subchondral plate micropicked to mimic microfracture used in the human. The implants were sutured in placed with uninterrupted sutures and the wound closed. For the group with the surgical defect only, the defect was left empty and the wound closed and treated as for the experimental groups. Elastic bandages were applied to the joint and joint motion reduced by using an external splint for 14 days. Topical anaesthesia was administered by analgesic patches 24 h before surgery and for 60 h after surgery. The animals were kept under observation and standard husbandry in a barn for the duration of the study. All procedures were carried out with the required ethical approvals The animals from each group were euthanased at 28 days or 4 months after surgery. At post mortem the treated joints were opened and examined macroscopically and the end of the femur removed and taken for photographic record and decalcification in preparation for histology. At the time of submission of this patent document the samples were still undergoing decalcification.

Example 1

Figure 2:
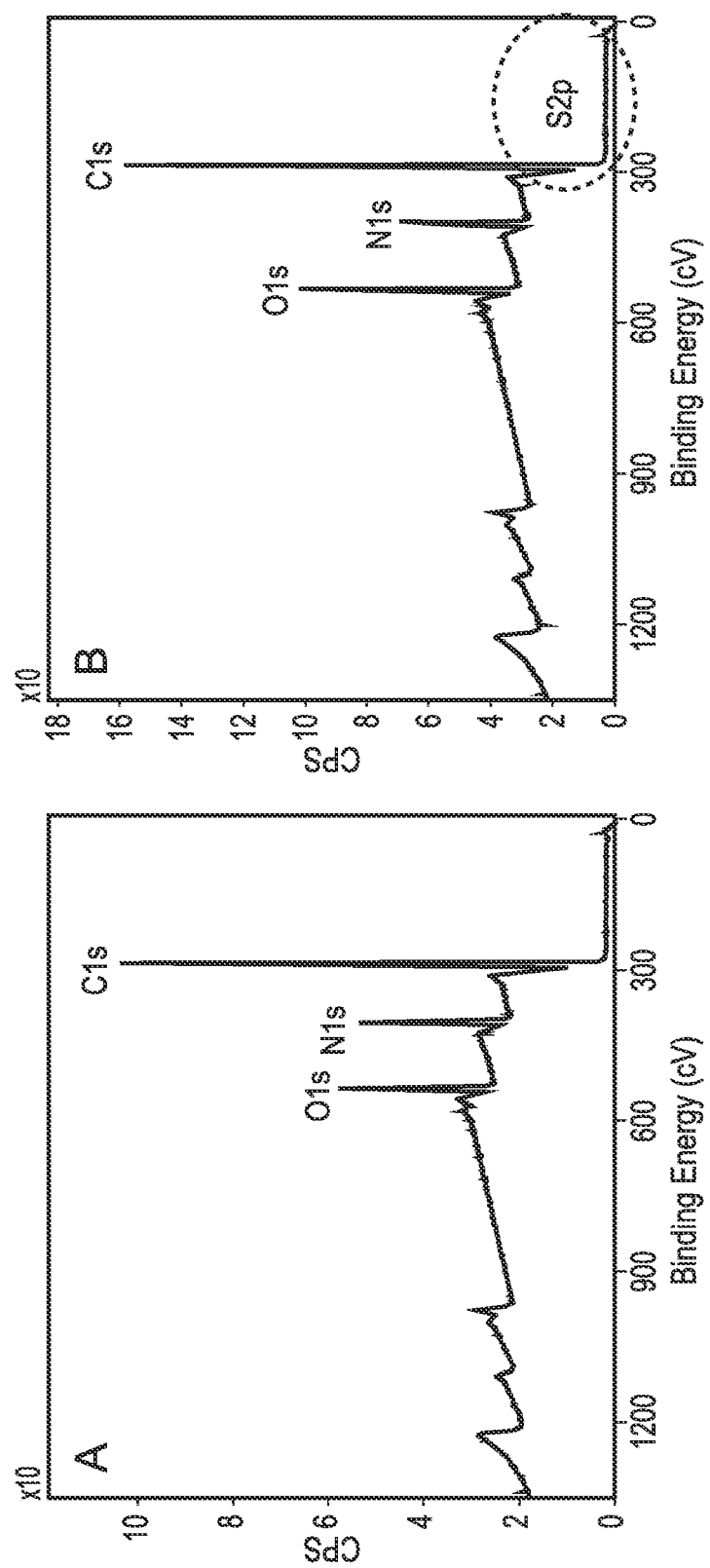
FIG. 2A shows a graph of the X-ray photon spectroscopy image of the allylamine-coated PLLA scaffold.
FIG. 2B shows the X-ray photon spectroscopy image of the heparin-treated, allylamine coated PLLA scaffold.
Figure 3:
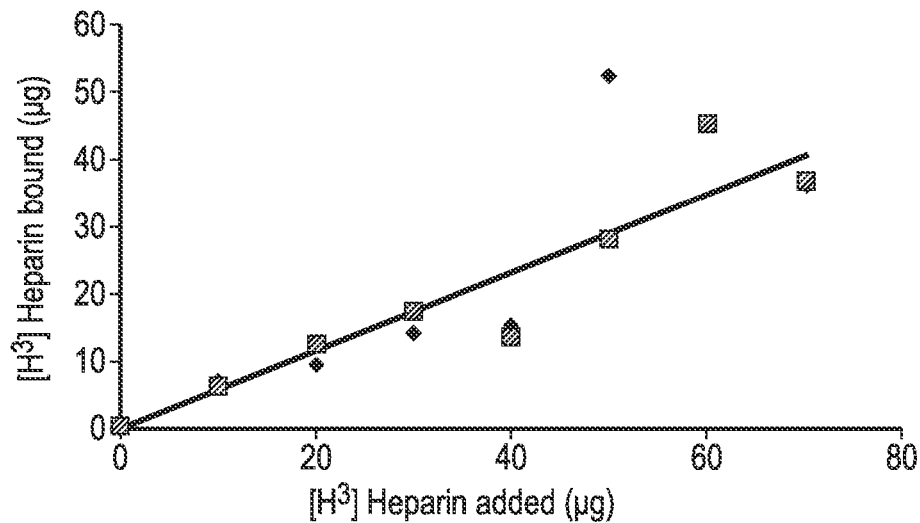
FIG. 3 shows a graph of the amount of $[H^3]$-radiolabelled heparin bound to the allylamine-treated scaffold vs the amount added.
Figure 4A:
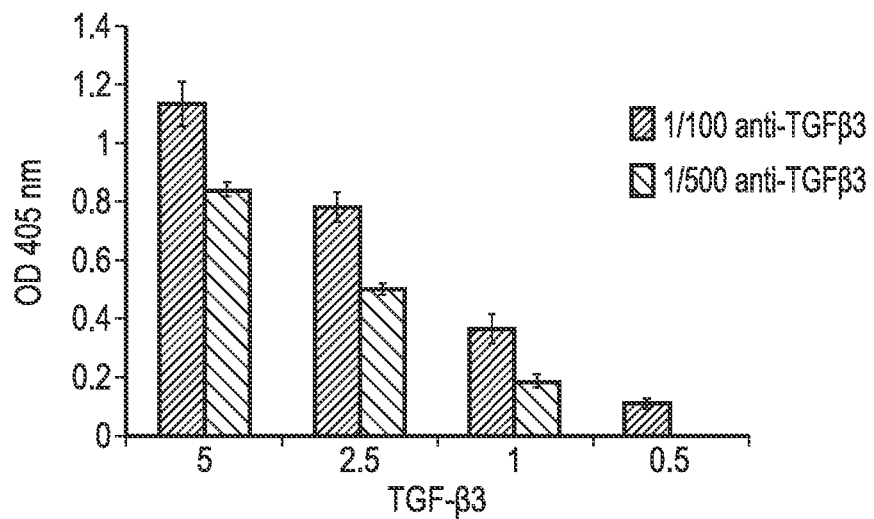
FIG. 4A shows the binding of TGFβ3 and FIG. 4B the binding of TGFβ1 to an allylamine and heparin-functionalised surface. Detection was by anti-TGFβ1 or anti-TGFβ3 antibodies.
Figure 4B:
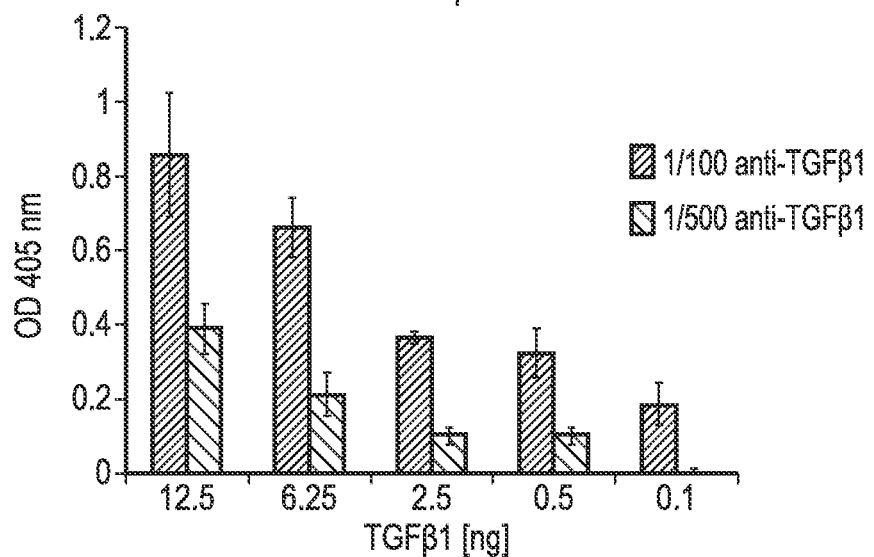
Figure 5A:
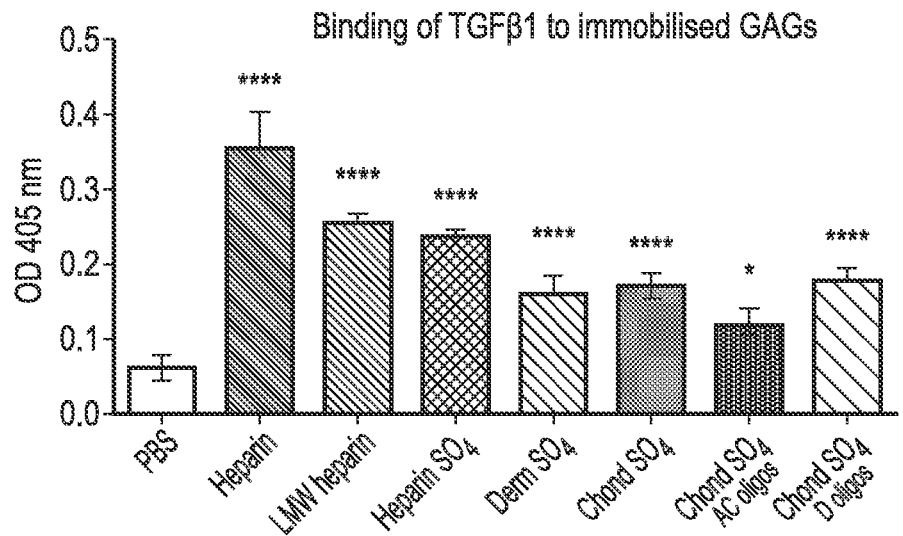
FIG. 5 shows various examples of bioactive factors binding to several example sulphated glycosaminoglycan oligosaccharides immobilised on an allylamine functionalised surface. Bioactive factors shown are TGFβ1 (FIG. 5A), TGFβ3 (FIG. 5B), CXCL12 (FIG. 5C), SDF1β (FIG. 5D), MIA (FIG. 5E), Wnt 3a (FIG. 5G) and BMP2 (FIG. 5H).
Figure 5B:
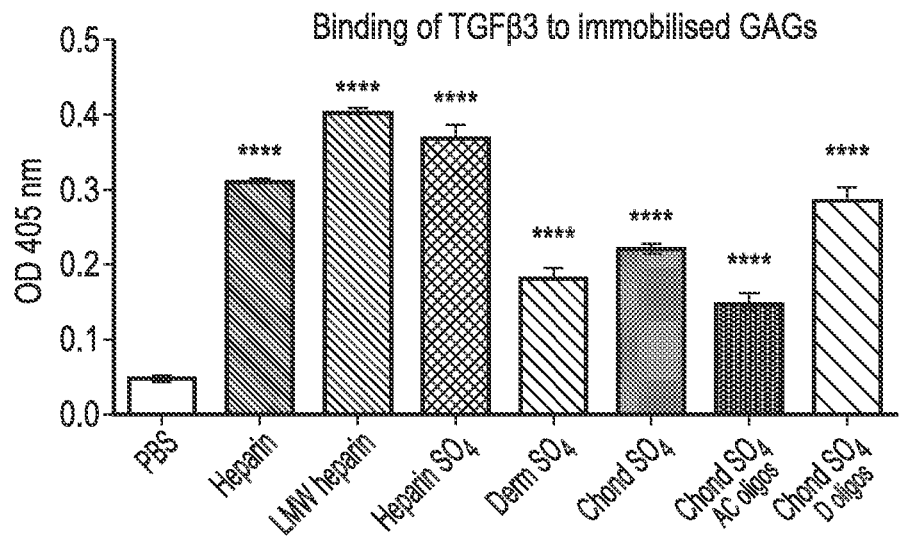
Figure 5C:
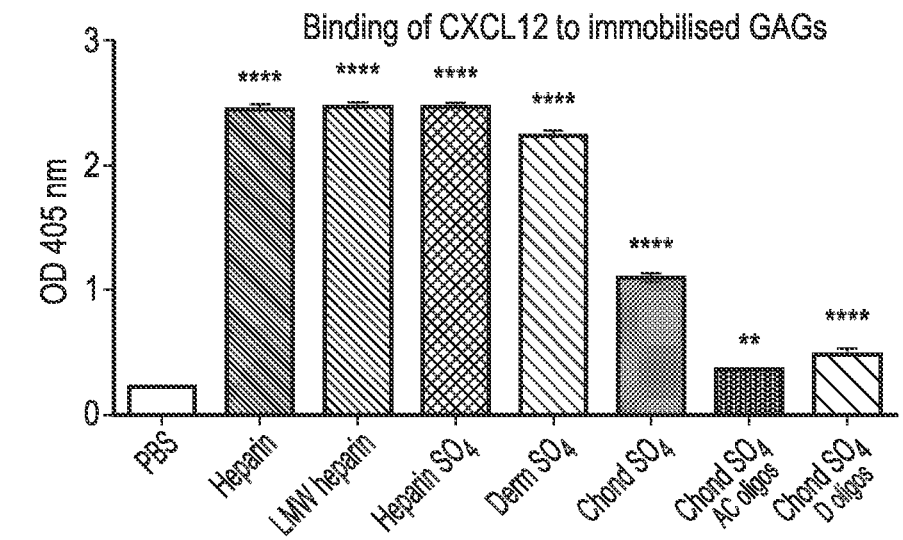
Figure 5D:
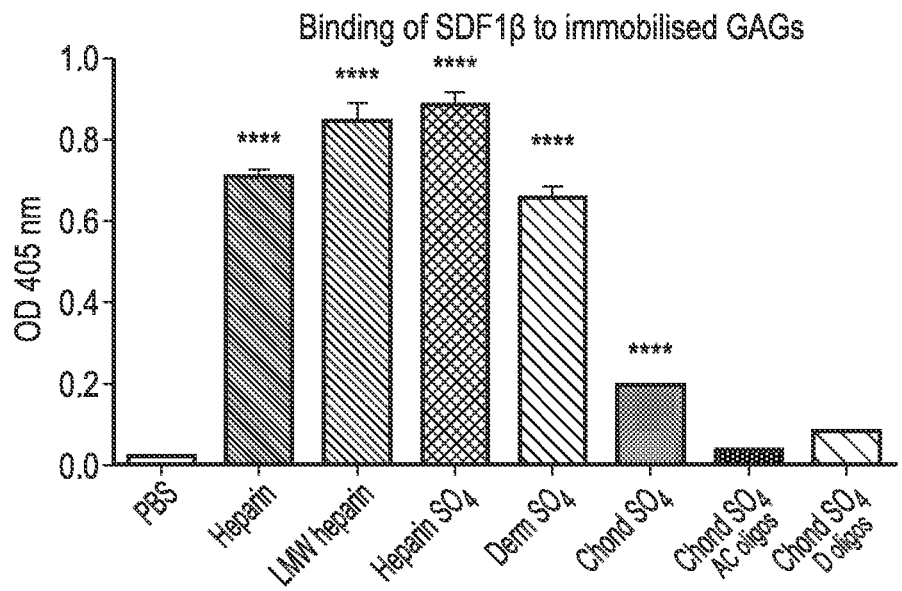
Figure 5E:
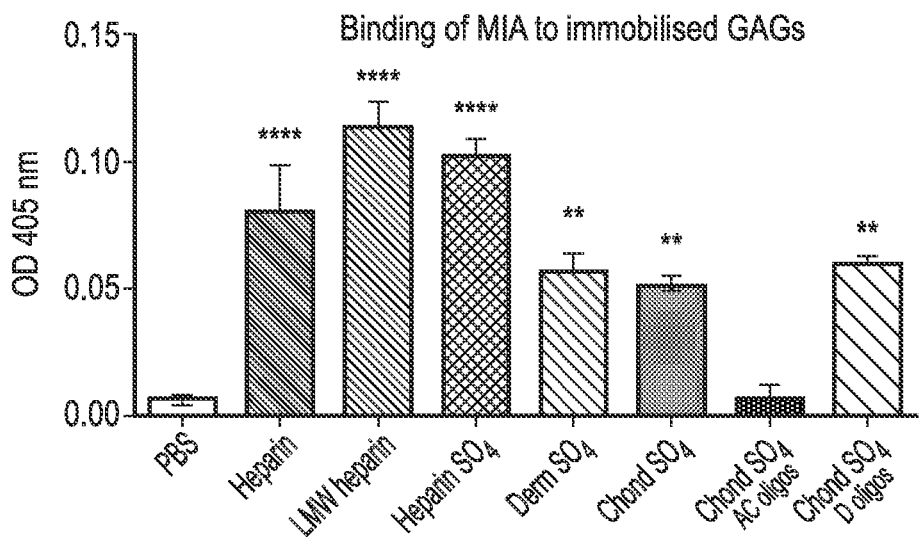
Figure 5F:
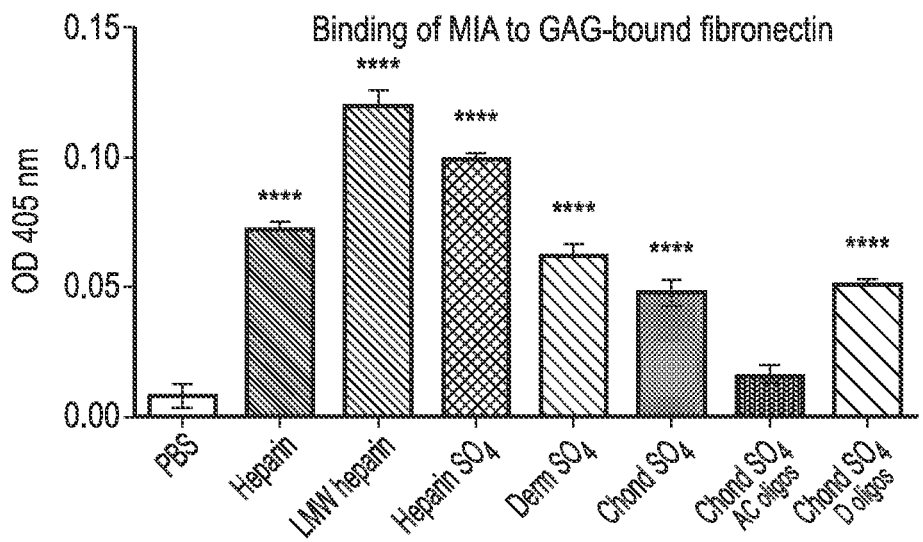
Figure 5G:
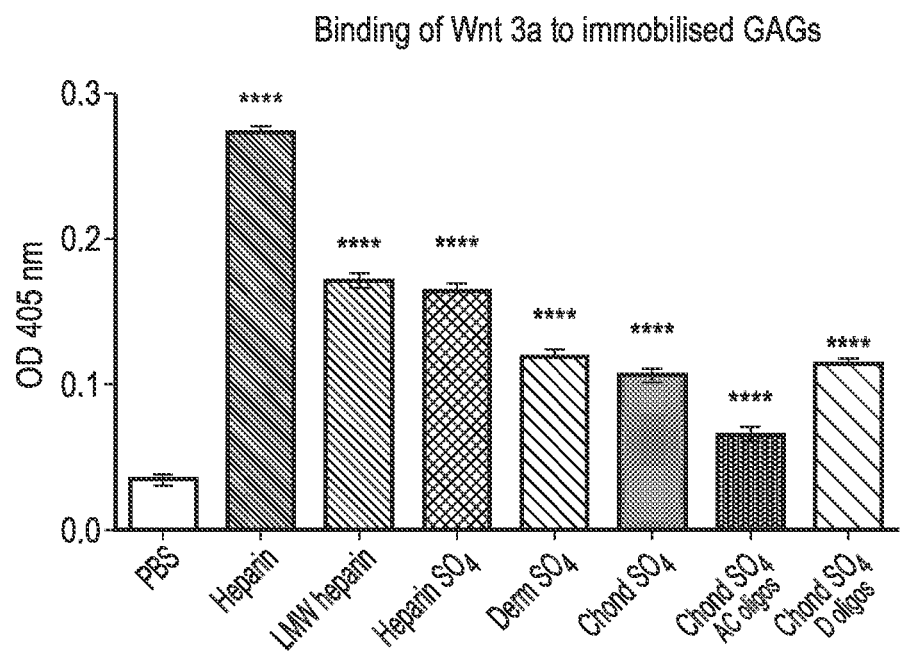
Figure 5H:
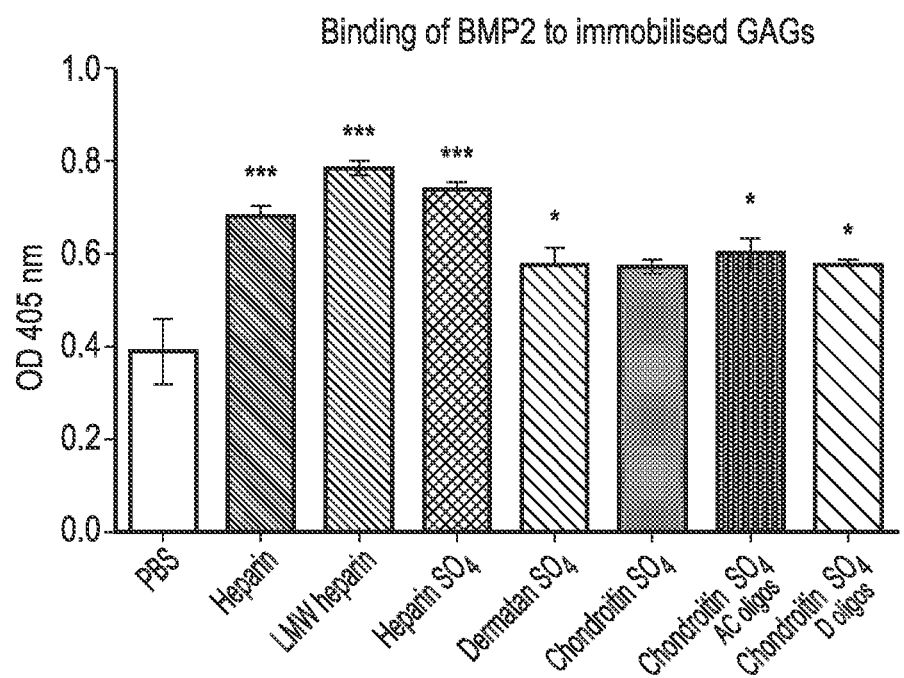

A PLLA scaffold was subjected to cold plasma treatment with allylamine as hereinbefore described and a coating of allylamine was confirmed by the presence of a nitrogen peak (FIG. 1D). FIG. 2B shows the X-ray photon spectroscopy image of the heparin-treated, allylamine coated PLLA scaffold. The small peak occurring at 168.1ev shows the presence of sulphur groups confirming binding of heparin to the allylamine-treated PLLA. FIG. 3 shows a linear relationship of the amount of [H$^3$]-radiolabelled heparin bound to the allylamine-treated scaffold vs the amount added The scaffold thus provides a positive surface coating of allylamine to which heparin binds non-covalently. Once the heparin has bound further experiments were conducted to show that heparin-binding bioactive factors such as for example TGFβ1, TGFβ3 and CXCl12 applied singularly or in combination will bind directly to the heparin layer by a tight non-covalent interaction. FIG. 4 shows the binding of TGFβ1 and TGFβ3 to an allylamine and heparin-functionalised surface. The presence of these bioactive factors was determined using immunolocalisation using rabbit polyclonal antibodies to TGFβ1 (ab92486, Abcam) and TGFβ3 (ab15537, Abcam). Bound anti-TGFβ antibodies were detected using a goat alkaline-phosphatase-labelled, polyclonal, secondary antibody to rabbit IgG (ab97072, Abcam). Results are the means+/−SD.

Example 2

FIG. 5 shows the binding of several example heparin-binding bioactive factors to various allylamine and glycosaminoglycan functionalised surface. The results show the means+/−standard error of the mean. We have demonstrated that TGFβ3 and TGFβ1, CXCL12, SDF1β, MIA, Wnt 3a and BMP2 bind to a selection of oligosaccharides directly. MIA is considered to bind to heparin via binding to fibronectin which will bind to heparin[41]. Here we have shown that MIA will bind directly to immobilised sulphated oligosaccharides as well as via binding to sulphated oligosaccharides via binding to fibronectin which then binds to the oligosaccharides. There are literature reports which state that TGFβ3 does not bind to sulphated oligosaccharides[56,58]. However, we have clearly demonstrated that TGFβ3 does bind directly to various sulphated glycosaminoglycans.

Binding of bioactive factors (BFs) which bind to GAG-binding proteins such as fibronectin or laminin, can be bound to the oligosaccharide-functionalised surface by first binding them to their oligosaccharide-binding protein partner (OBPP) such as fibronectin and then applying the biological factor—OBPP combination to the oligosaccharide-functionalised surface. An example of this type of BF-binding to oligosaccharides is demonstrated in FIG. 5F which shows the binding of MIA to fibronectin immobilised on a surface functionalised with sulphated oligosaccharides Example 3

Figure 6:
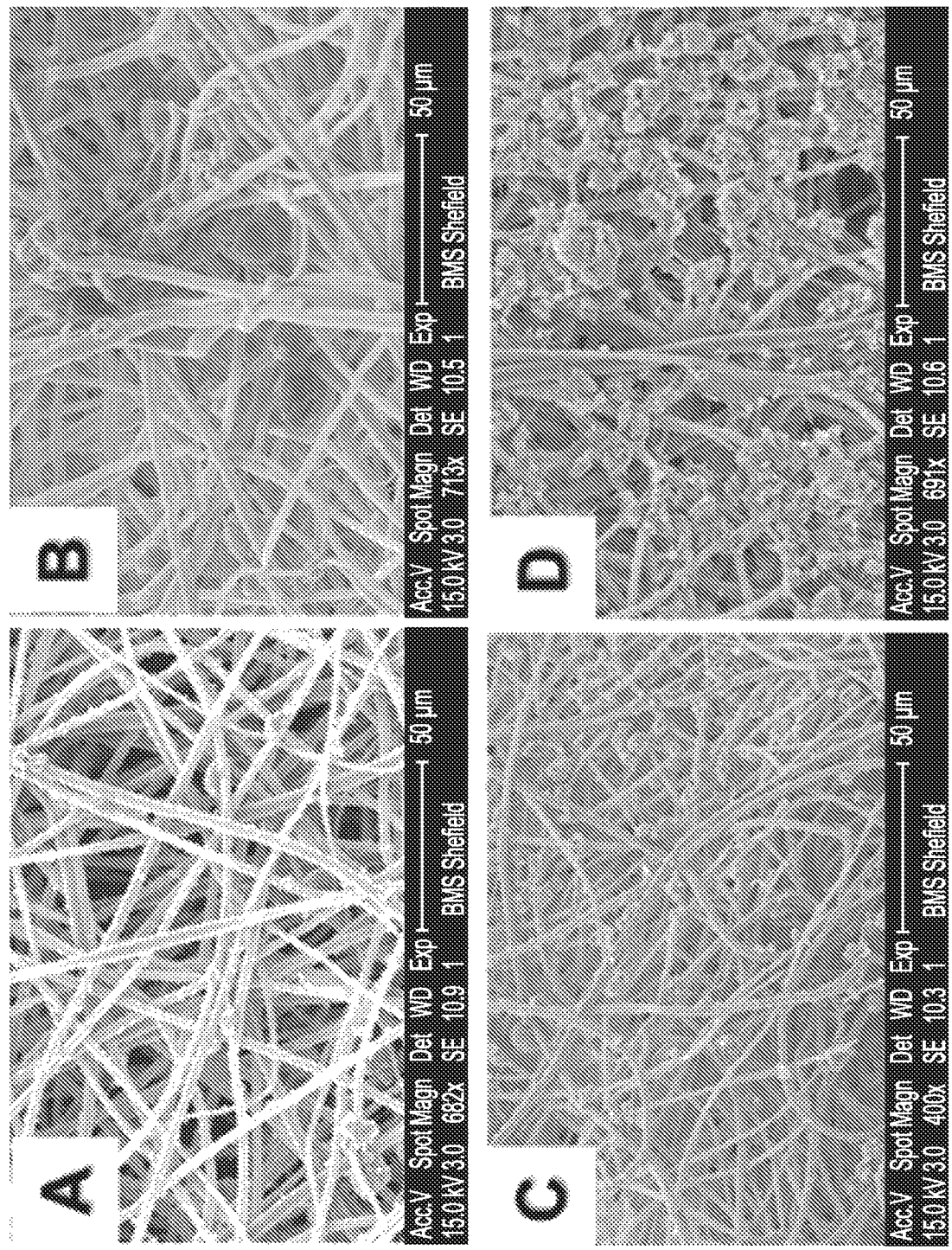
FIG. 6 shows an example of the attachment of mesenchymal stem cells to control (PLLA) and scaffolds functionalised with the example chondrogenic BF, TGFβ3.
Figure 7:
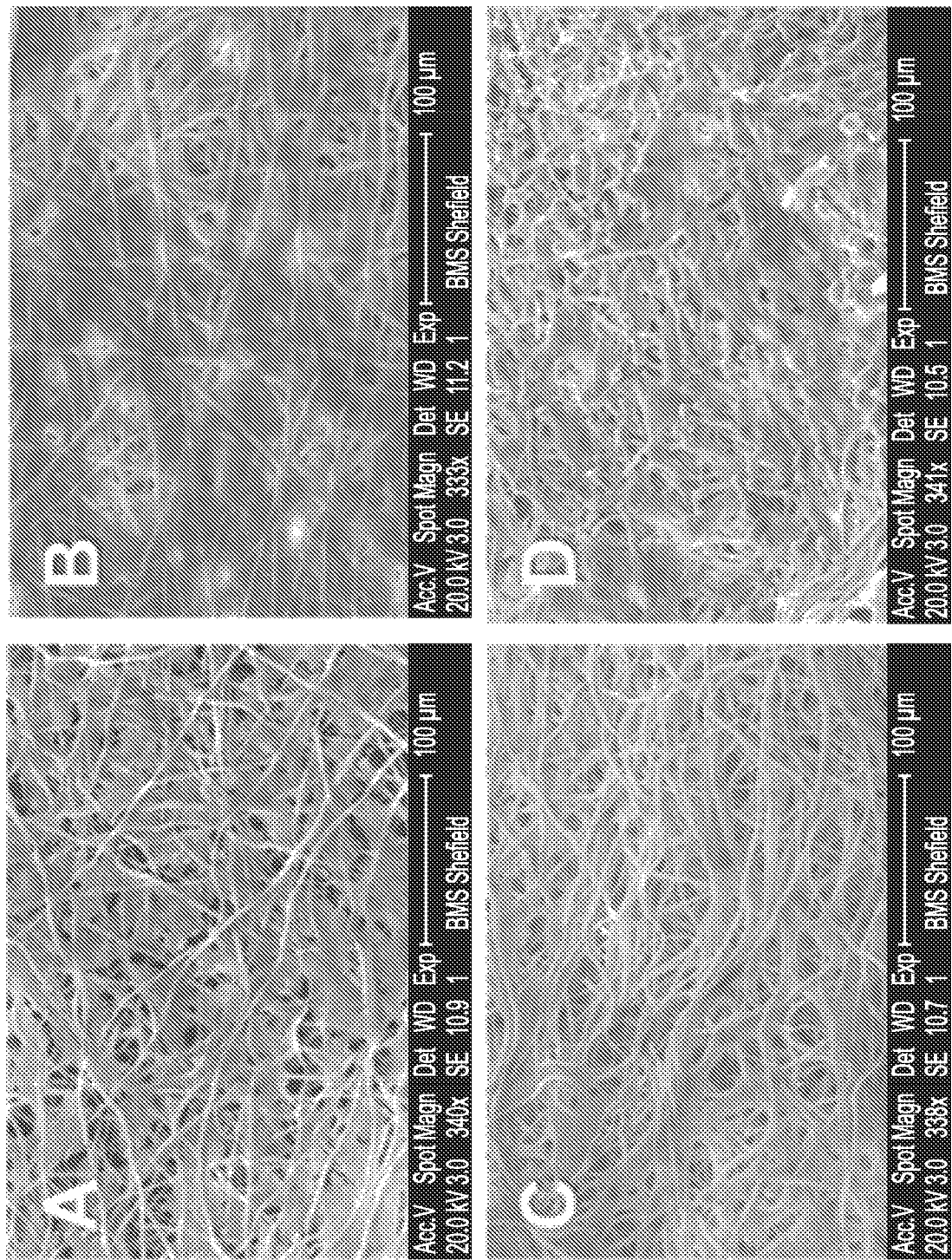
FIG. 7 shows an example of the attachment of bovine chondrocytes to PLLA and PLLA scaffolds functionalised with the example chondrogenic BF, TGFβ3.

Studies were undertaken with bovine synovial fluid mesenchymal stem cells (SF-MSCs) or chondrocytes to investigate the attachment of the cells to an example of PLLA scaffolds functionalised with an example chondrogenic BF. Results for the SF-MSCs are shown in FIG. 6 and results for chondrocytes in FIG. 7. Cells were seeded onto the scaffolds as described herewithin and 48 hr after seeding the cell-scaffold constructs were fixed and examined by scanning electron microscopy. FIGS. 6 and 7 show scanning electron micrographs of SF-MSCs and chondrocytes attached to PLLA. (FIGSS. 6A 7A) and PLLA scaffolds functionalised with allylamine (FIGS. 6B and 7B), heparin (FIGS. 6C and 7C) and TGFβ3 (FIGS. 6D and 7D). For both cell types, TGFβ3-functionalised PLLA scaffolds showed a greater density of cells bound than allylamine or heparin functionalised PLLA scaffolds or unmodified PLLA. In summary, this data shows that MScs and chondrocytes can attach to PLLA scaffolds in higher cell densities on PLLA functionalised with TGFβ3 compared to non-functionalised PLLA or PLLA functionalised with heparin-only or allylamine-only.

Example 4

Figure 8A:
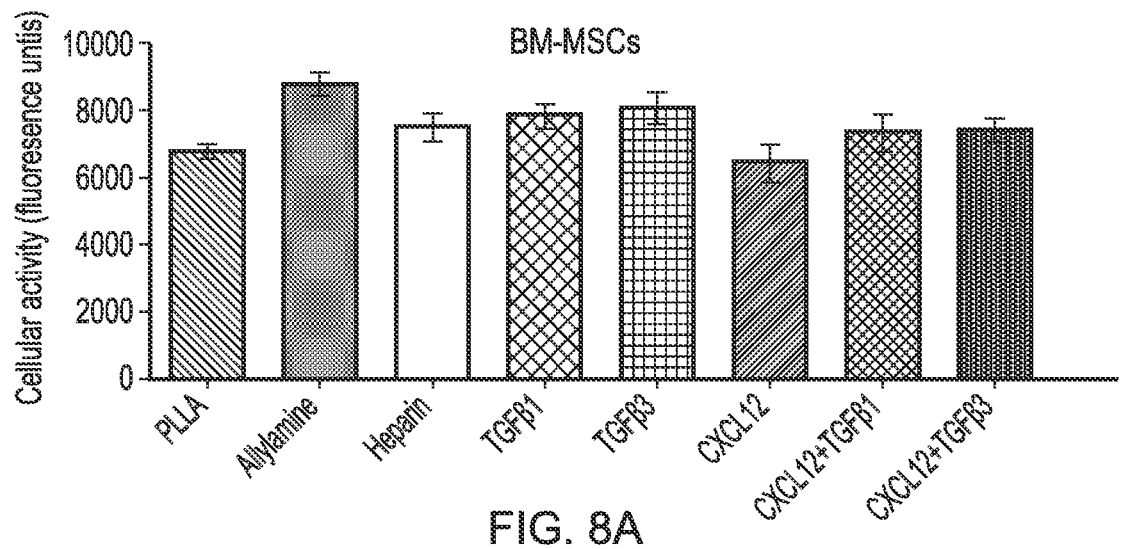
FIGS. 8A-8E demonstrate the viability of various skeletal tissue cells cultured on scaffolds functionalised with one or more growth factors. The examples shown are mesenchymal stem cells derived from bone marrow (bone-marrow-derived mesenchymal stem cells, BM-MSCs) or joint fluid (synovial mesenchymal stem cells, SF-MSCs), ligament cells (ligamentocytes), chondrocytes and bone (MG 63 osteoblastic cells).
Figure 8B:
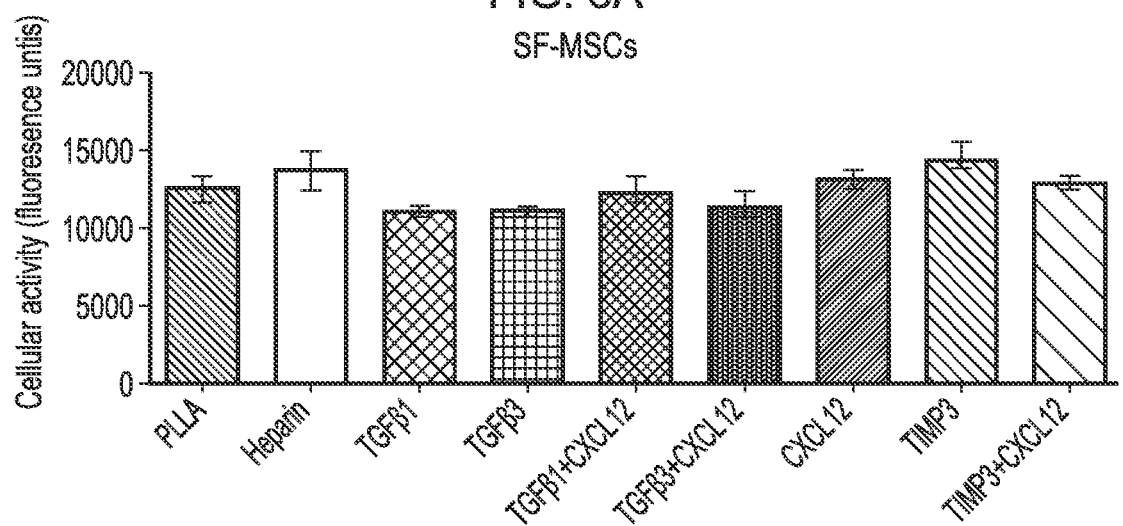
Figure 8C:
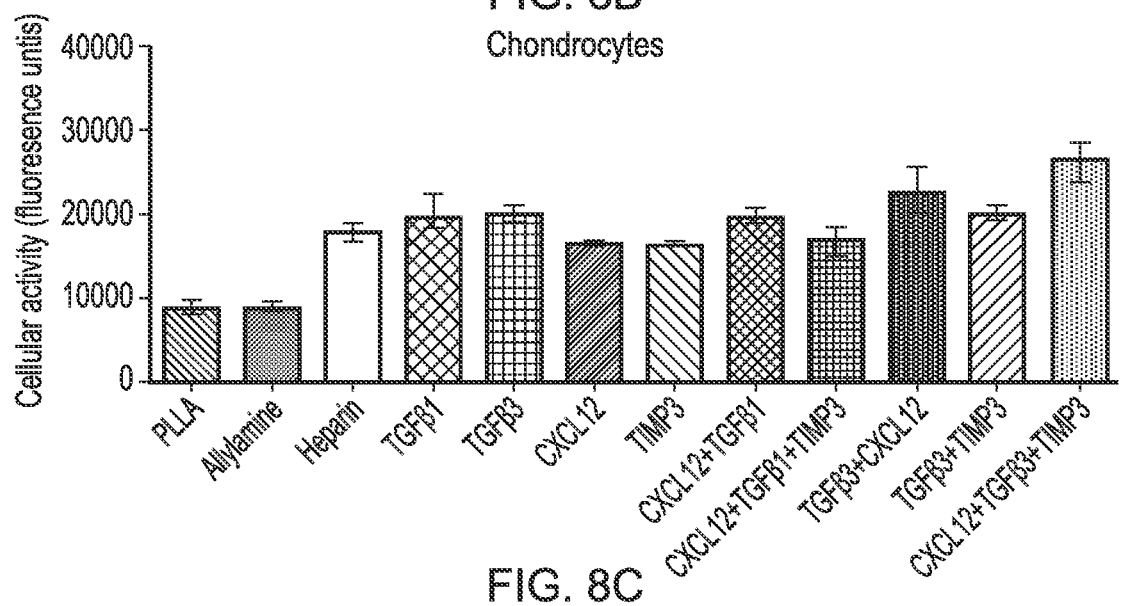
Figure 8D:
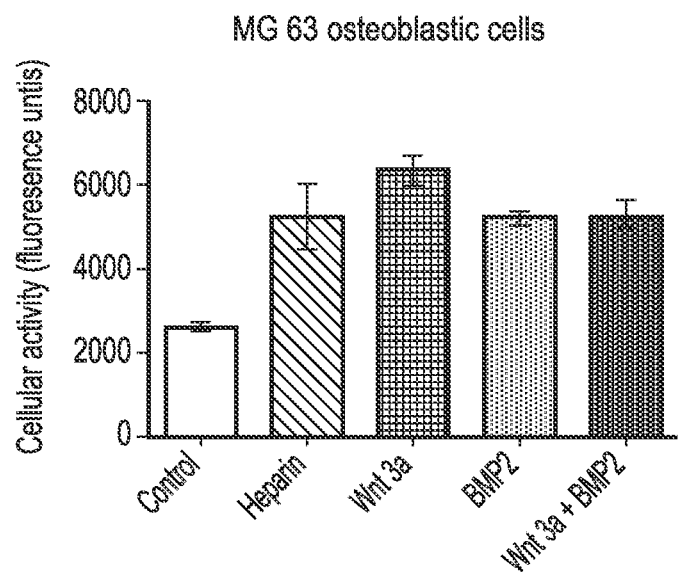
Figure 8E:
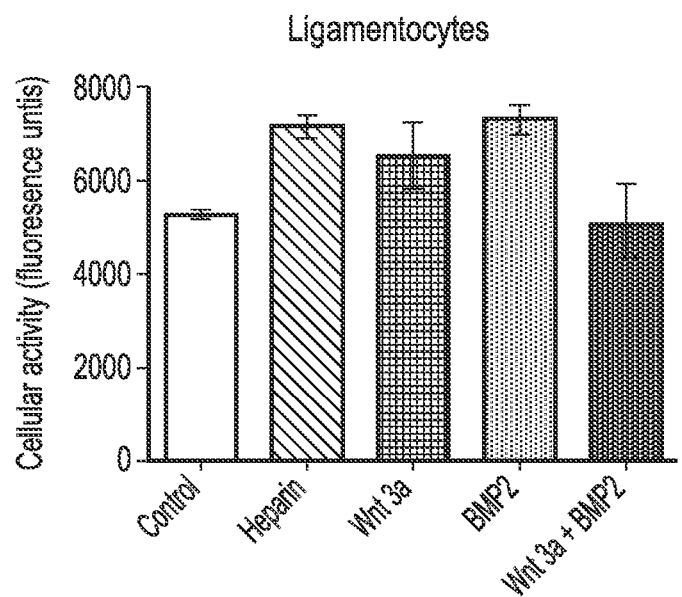
Figure 9:
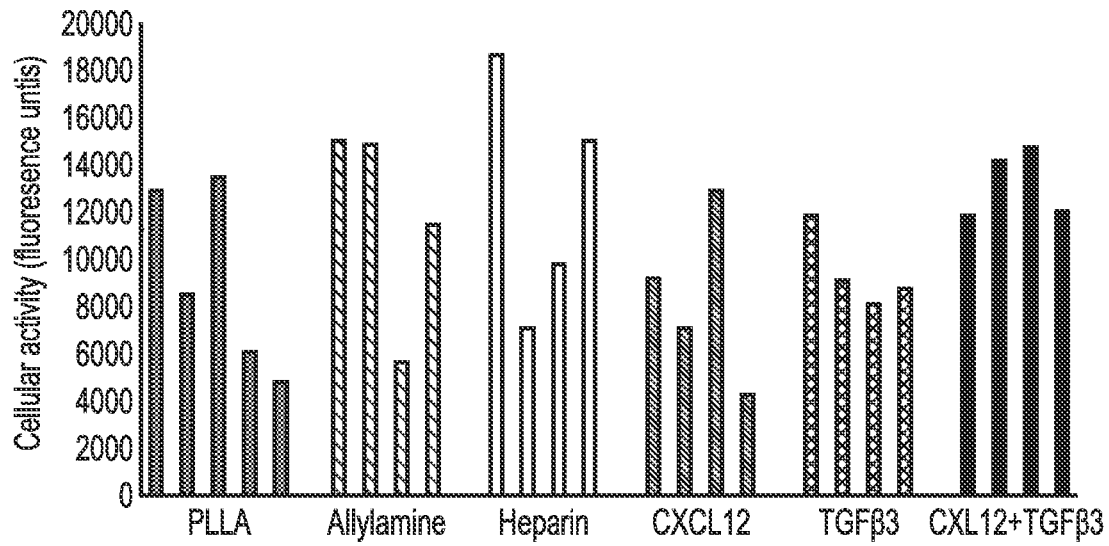
FIG. 9 shows the individual experimental cell viability results for bone marrow mesenchymal stem cells cultured on the control (PLLA) and functionalised scaffolds. It is observed that the experimental variability in the results is reduced in the scaffolds functionalised with both CXCL12 and TGFβ3 which is an indication of a more even cell attachment to the scaffolds in this group. The cells were cultured in basal medium in the absence of serum or additional growth factors. Each bar represents a single experiment.

FIGS. 8A to 8E show the cell viability of human bone-marrow derived mesenchymal stem cells (BM-MSCs, FIG. 8A), synovial fluid-derived mesenchymal stem cells (SF-MSCs, FIG. 8B), bovine articular chondrocytes (FIG. 8C), human MG63 osteoblastic cells (8D) and human ligamentocytes (FIG. 8E) cultured on various biological factor-functionalised PLLA scaffolds. These scaffolds were functionalised with examples of classical chondrogenic and collagen-stimulating BFs (e.g. TGFβ), chemotactic (e.g. CXCL12), protease inhibitor (e.g. TIMP3) and osteoblastic factors (e.g. Wnt 3a). FIGS. 8D, 8E and 8F show respectively BM-MSCs, ligamentocytes and MG63 osteoblastic cells cultured on Wnt 3A and BMP2-functionalised scaffolds under basal culture conditions. These bioactive factors are example osteogenic factors. All scaffolds showed good biocompatibility; all the cell types used showed viable cells on the various biological factor-functionalised scaffolds (determined using the vital dye PrestoBlue® described herein) which were maintained throughout the culture period (from 0-42 days) without exogenous addition of growth factors or serum. Cell viability on PLLA functionalised with allylamine only or heparin or BFs was not statistically different from the PLLA control or enhanced above that of the PLLA controls FIG. 8 demonstrates that mesenchymal stem cells, cartilage, bone and ligament-derived cell types can successfully be cultured on the functionalised scaffolds and remain viable. We have also demonstrated (FIG. 9) that mesenchymal stem cells (MSCs) can bind to PLLA scaffolds functionalised with a combination of the growth factor TGFβ3 and chemokine CXCL12 in nanogram amounts provided less variability in seeding efficacies (as indicated by the PrestoBlue® assay described herewithin) than when the cells were seeded onto PLLA or PLLA functionalised with just allylamine, or heparin, or TGFβ1 or TGFβ3 alone. FIG. 9 shows cell viability of individual cell/scaffold constructs 48 hr after seeding the scaffolds with human mesenchymal stem cells. Cell viability was assessed by the Prestoblue® assay described hereinbefore. All scaffolds were biocompatible. The scaffolds functionalised with a combination of CXCL12 and TGFβ3 showed less variability in the cellular activity of the MSC/scaffold constructs (FIG. 9) compared to the PLLA and the other functionalised scaffolds (allylamine, heparin, CXCL12, TGFβ3). This is an indication of the more even seeding of MSCs observed on the scaffolds functionalised with the combination of CXCL12 and TGFβ3.

Example 5

Figure 10A:
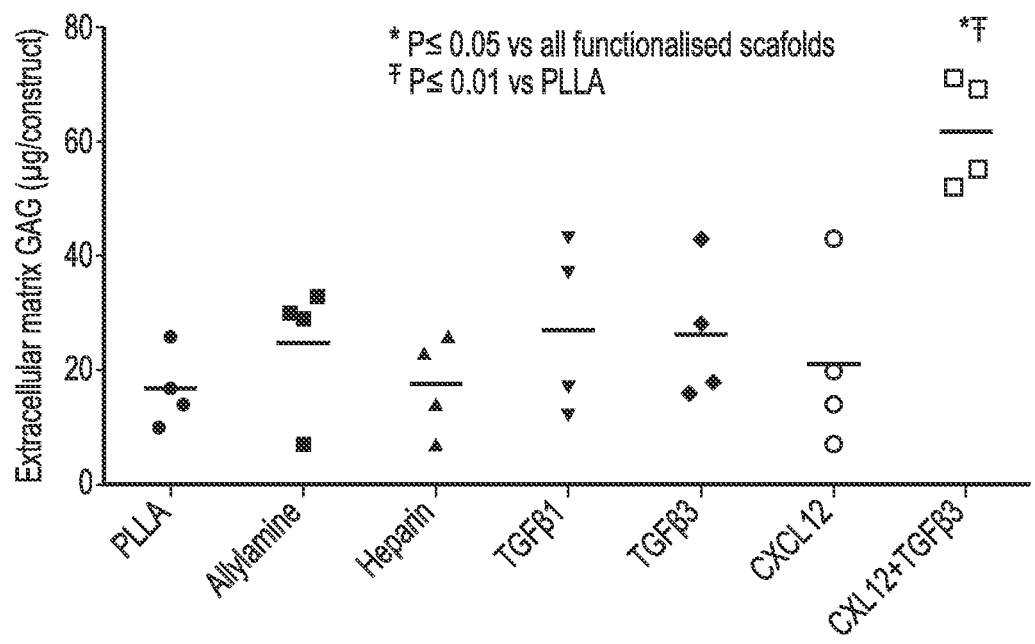
FIGS. 10A and 10B shows the extracellular matrix (ECM) proteoglycan accumulation [measured as the amount of ECM glycosaminoglycans (GAG)] by constructs formed from human bone marrow-derived MSCs cultured on the control PLLA scaffolds and the functionalised scaffolds. The cells were cultured in basal medium in the absence of serum or additional growth factors.

Extracellular matrix (ECM) accumulation by constructs formed from human bone marrow-derived MSCs cultured on the functionalised scaffolds compared to constructs formed from the cells cultured on PLLA was examined. The cell/scaffold constructs were incubated for 33 days in a basic, growth factor-free medium of DMEM containing 1 mg/ml BSA, $10^{-7}$M dexamethasone, ITS (10 µg/ml insulin, 5.5 µg/ml transferrin, 0.5 µg/ml selenium, 4.7 µg/ml each of linoleic and oleic acids) and 25 µg/ml L-ascorbic acid. The proteoglycan content of the ECM was determined by quantifying the glycosaminoglycan (GAG) content of the constructs using 1,9-dimethylmethylene blue as described above. Results (FIG. 10A) show the GAG content of individual constructs and the mean value for each experimental group. A combination of CXCL12 and TGFβ3 gave the highest level of GAG accumulation ($P \leq 0.05$ against all scaffolds, $P \leq 0.01$ against PLLA) compared to constructs formed on scaffolds functionalised with TGFβ or CXCL12 alone or with just allylamine or heparin-functionalisation. Constructs formed on PLLA functionalised with a combination of CXCL12 and TGFβ3 also showed the least variability in GAG accumulation per construct reflecting a more uniform cell seeding compared to all other scaffold groups.

Figure 10B:
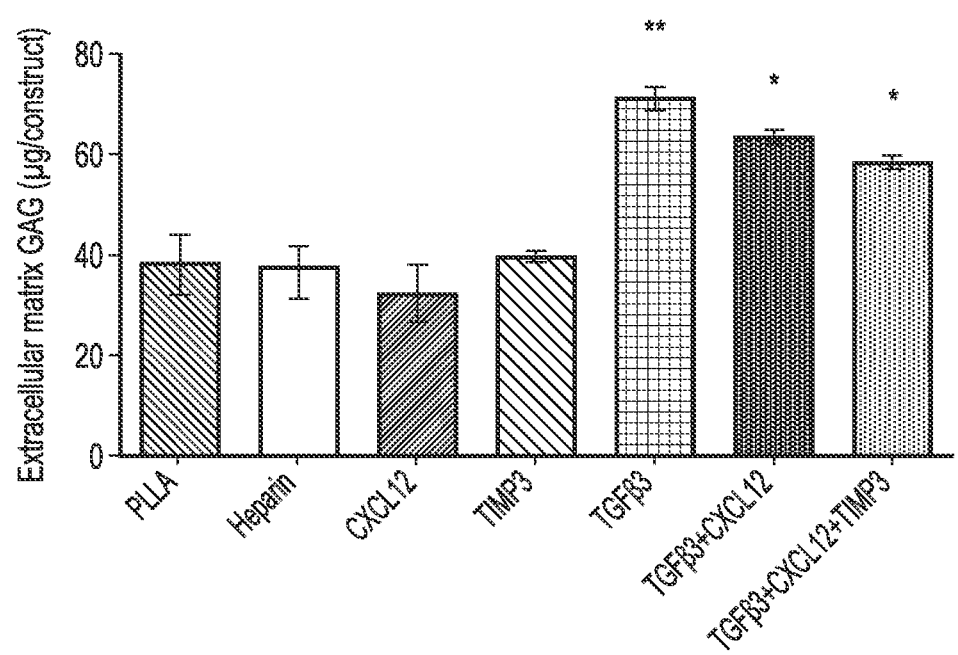

FIG. 10B shows the GAG content of human BM-MSCs cultured for 44 days on BF-functionalised scaffolds compared to PLLA. The constructs were incubated in the absence of serum or added growth factors using the basic medium described above. The scaffold groups of TGFβ3, TGFβ3+CXCL12 and the group TGFβ3+CXCL12+TIMP3, gave significantly greater levels of ECM GAG content compared to the controls (*p≥0.05. **p≤3.01) Therefore even after over a 6 week extended culture period in the absence of added growth factors, some BFs and BF combinations show enhanced ECM accumulation over PLLA or PLLA functionalised with heparin only.

Figure 11A:
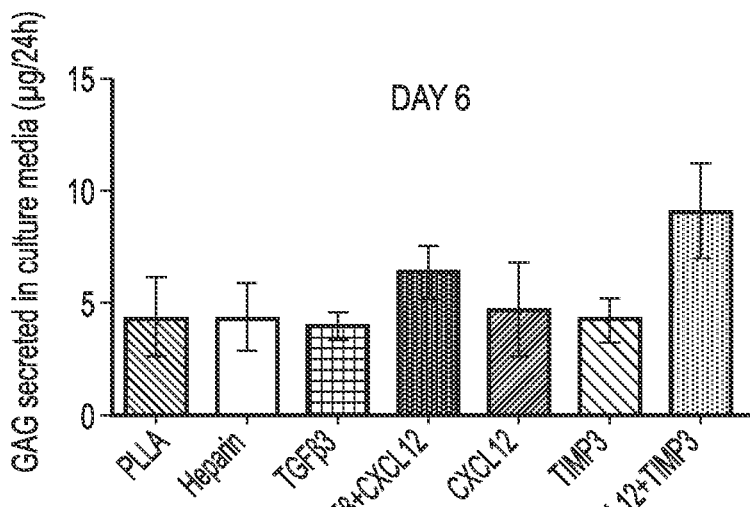
FIG. 11A shows the rate of accumulation of GAG between days 2-6 of culture of the cell-scaffold constructs.
Figure 11B:
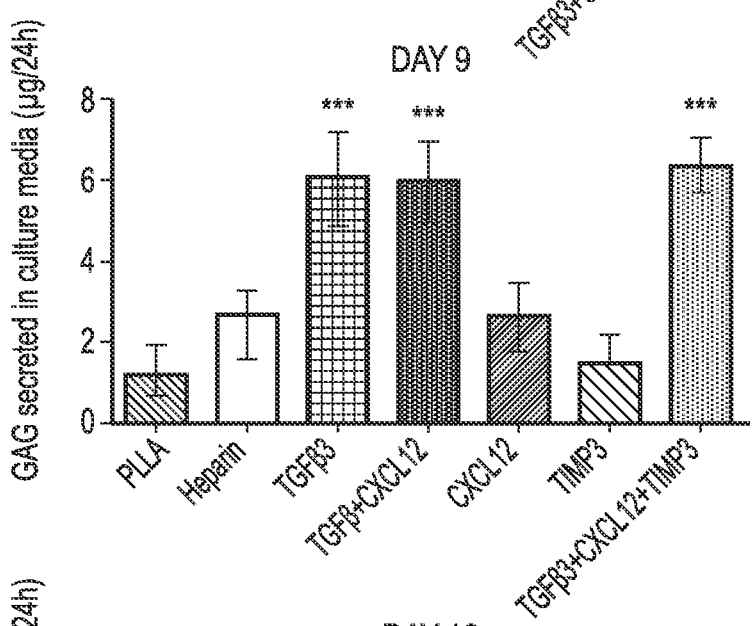
FIG. 11B shows the accumulation rate between days 6-9 of culture of the cell-scaffold constructs and FIG. 11C shows the rate of GAG accumulation between days 12-16 of the cell-scaffold constructs. It is seen that by day 9 of culture, cells cultured on the scaffolds functionalised with TGFβ3, TGFβ3+CXCL12 combination and TIMP3+TGFβ3+CXCL12 show an increase in GAG accumulation compared to PLLA. By day 16 cells cultured on all the functionalised scaffolds (with the exception of the heparin-only functionalised scaffold) showed greater GAG accumulation compared to cells on PLLA scaffolds. The cells were cultured in basal medium in the absence of serum or additional growth factors. Results are the mean+/−SEM.
Figure 11C:
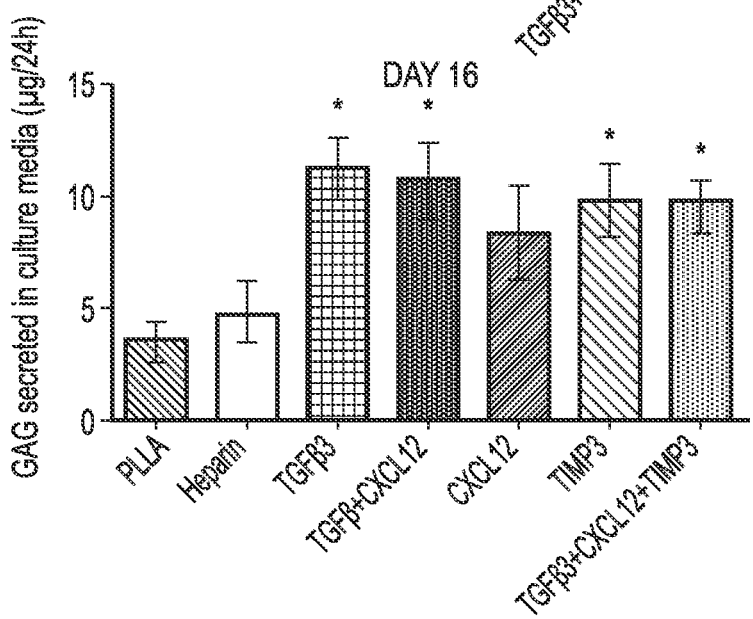

Measurement of GAGs in the culture media from MSCs grown on the functionalised scaffolds was carried out to monitor likely chondrogenic differentiation of the stem cells. FIG. 11 shows the rate of production of GAG into the culture media at day 6 (FIG. 11A), day 9 (FIG. 11B) and 16 (FIG. 11C) after seeding the cells on the scaffolds. By day 9 (FIG. 11B) a significant increase in the rate of GAG secretion was observed only for MSCs cultured on TGFβ3 functionalised scaffolds, or combinations of TGFβ3 and CXCL12 or TGFβ3 and CXCL12 and TIMP3, By day 16 after seeding FIG. 11C) all the functionalised groups (except those with heparin-functionalised scaffolds) showed increased GAG production compared to the PLLA control. Therefore, these results demonstrate that MSCs cultured on TGFβ3 functionalised scaffolds, or combinations of TGFβ3 and CXCL12 or TGFβ3 and CXCL12, had undergone chondrogenic differentiation earlier (by day 9), even in the presence of $10^{-7}$M dexamethasone, compared to the PLLA controls or heparin-only functionalised scaffold.

In summary these data show that the BF-functionalised scaffolds have biological activity and support MSC attachment, viability, chondrogenic differentiation and extracellular matrix formation.

Example 6

Figure 12:
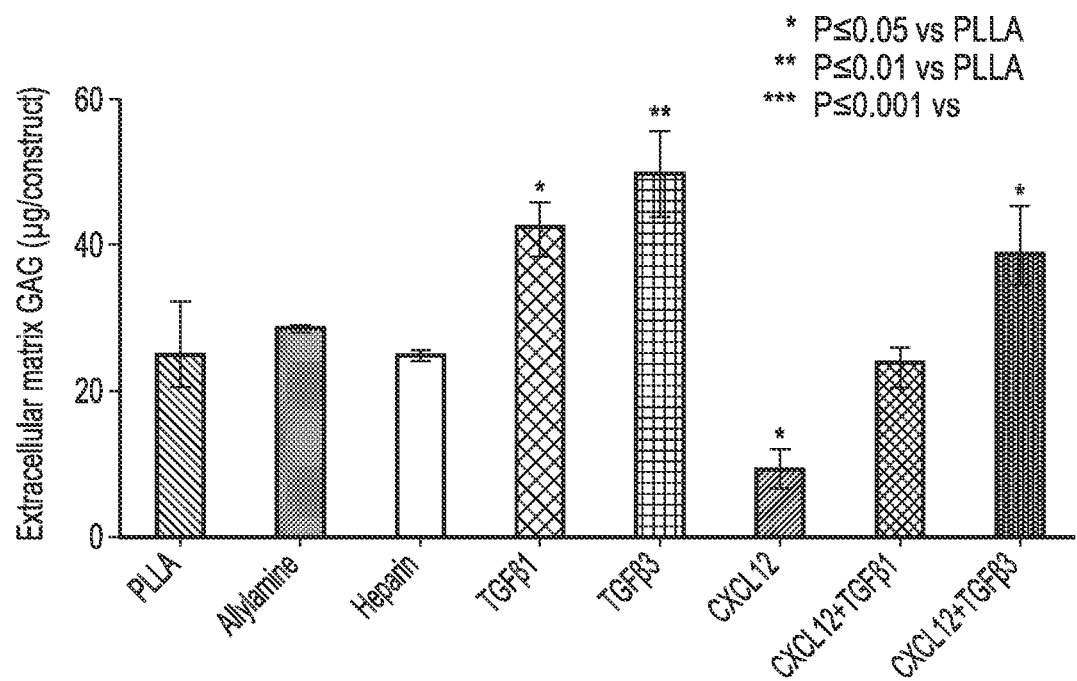
FIG. 12 shows extracellular matrix (ECM) accumulation by constructs formed from bovine articular chondrocytes and cultured on the control PLLA scaffolds and the functionalised scaffolds. The cells were cultured in basal medium in the absence of serum or additional growth factors. Results are the mean+/−standard deviation.

Scaffolds were functionalised with example chondrogenic (for example TGFβ1 and TGFβ3) and cell homing (for example CXCL12) BFs. Extracellular matrix (ECM) accumulation by constructs formed from bovine articular chondrocytes seeded onto functionalised scaffolds were compared to constructs formed from chondrocytes seeded onto PLLA. The cell/scaffold constructs were incubated for 28 days in a basic, growth factor-free medium of DMEM containing 1 mg/ml BSA, $10^{-7}$M dexamethasone, ITS (10 μg/ml insulin, 5.5 μg/ml transferrin, 0.5 μg/ml selenium, 4.7 μg/ml each of linoleic and oleic acids) and 25 μg/ml L-ascorbic acid. The proteoglycan content of the ECM was determined by quantifying the glycosaminoglycan (GAG) content of the constructs using 1,9-dimethylmethylene blue as described above. Results shown in FIG. 12 are the means+/− standard deviation. TGFβ1- and TGFβ3-functionalised scaffolds gave constructs with significantly greater levels of ECM GAGs than PLLA scaffolds (p≤0.01 and p≤0.001 respectively. CXCL12-functionalised scaffolds were found to significantly inhibit ECM GAG incorporation (P≤0.01). Scaffolds functionalised with a combination of CXCL12 and TGFβ1 did not yield constructs with ECM GAG levels greater than PLLA-based constructs. In contrast, TGFβ3 could overcome inhibition of ECM formation caused by CXCL12. TGFβ1 and TGFβ3 are often assumed to have very similar activities in the scientific literature. However, it is clear that TGFβ1 and TGFβ3 in combination with CXCL12 have differing effects on chondrocytes. Scaffolds functionalised with a combination of CXCL12 and TGFβ3 showed significant ECM GAG accumulation over PLLA-based constructs (P≤0.05). FIG. 12A shows that after 44 days of culture in basal medium without added growth factors or serum, the effect of the functionalised scaffolds in terms of extracellular matrix GAG incorporation, still remained significantly greater than the PLLA control or the heparin-only functionalised scaffold.

Figure 13A:
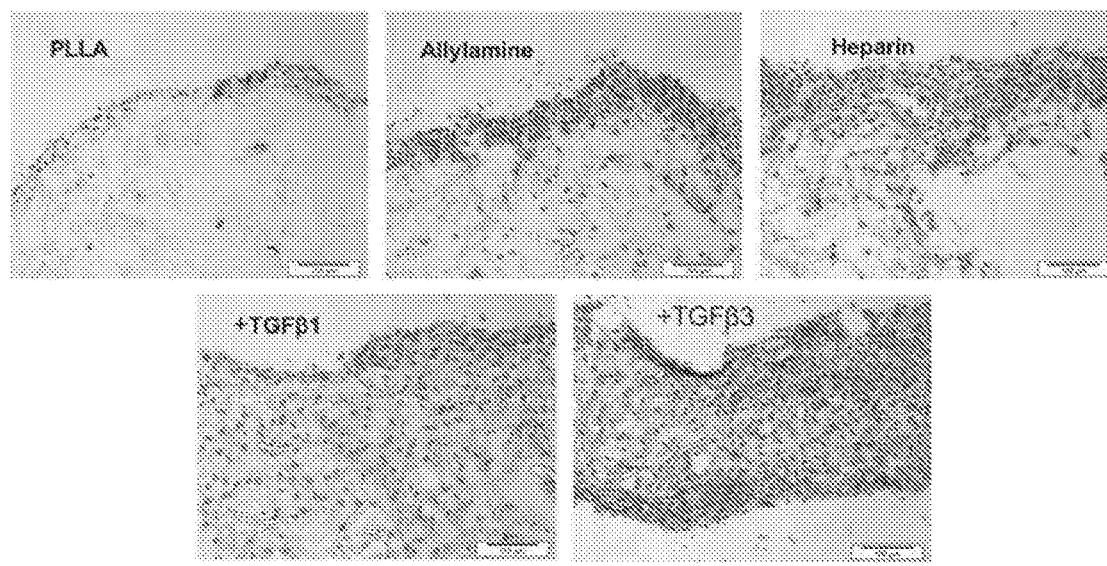
FIG. 13A shows immunolocalisation of collagen II in chondrocytes cultured on PLLA and PLLA functionalised with allylamine only, heparin, TGFβ1 and TGFβ3.
Figure 13B:
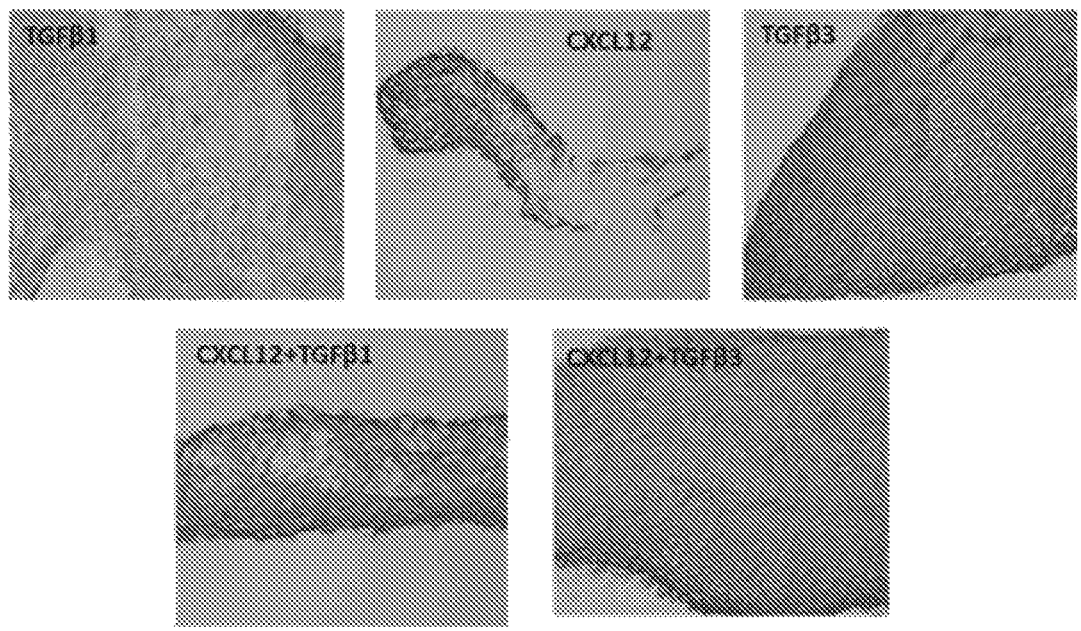
FIG. 13B shows immunolocalisation of collagen II in constructs formed from bovine articular chondrocytes and PLLA functionalised with TGFβ1, TGFβ3, CXCL12 or combinations of CXCL12 and TGFβ1 or CXCL12 and TGFβ3. All images are taken at magnification of ×20.

The effect of the functionalised scaffolds on chondrocyte phenotype was investigated. Collagen II deposition in the ECM is a well-known chondrogenic marker indicative a differentiated chondrocyte phenotype. FIG. 13 shows histological sections of constructs and immunolocalisation of collagen II in the constructs formed from bovine articular chondrocytes and PLLA or chondrocytes and functionalised scaffolds of PLLA. Functionalisation of the PLLA with TGFβ1 or TGFβ3 resulted in a greater density of chondrocytes distributed throughout the scaffold and extensive formation of collagen II as shown in FIG. 13A. FIG. 13B shows immunolocalisation of collagen II in constructs formed from bovine articular chondrocytes and PLLA functionalised with TGFβ1, TGFβ3, CXCL12 or combinations of CXCL12 and TGFβ1 or CXCL12 and TGFβ3. Alone, CXCL12 functionalised scaffolds yielded little volume of extracellular matrix and less collagen II deposition. Also, scaffolds functionalised with CXCL12 in combination with TGFβ1 gave much less volume of ECM and collagen II deposition compared to that observed with TGFβ1 alone. However, in contrast, scaffolds functionalised with a combination of CXCL12 and TGFβ3 when seeded with chondrocytes, gave cell/scaffold constructs with good extracellular matrix formation and extensive collagen II deposition compared to that seen with chondrocytes cultured on unmodified PLLA or PLLA functionalised with only allylamine or heparin. These results were not expected and show that the composition of BFs used for functionalisation is important. Scaffolds functionalised with TGFβ1 and CXCL12 could potentially lead to temporary inhibition of cartilage matrix synthesis in the medical device. In contrast, scaffolds functionalised with a combination of TGFβ3 and CXCL12 should promote good cartilage matrix within the medical device. This example also demonstrates that members of the TGFβ group of BFs may give different biological effects in different tissues. This is rarely considered in the scientific literature.

In summary, these data show that BF-functionalised scaffolds can support chondrocyte attachment and cell viability, and chondrocyte differentiation/maintenance of the chondrogenic phenotype Example 7

Figure 14:
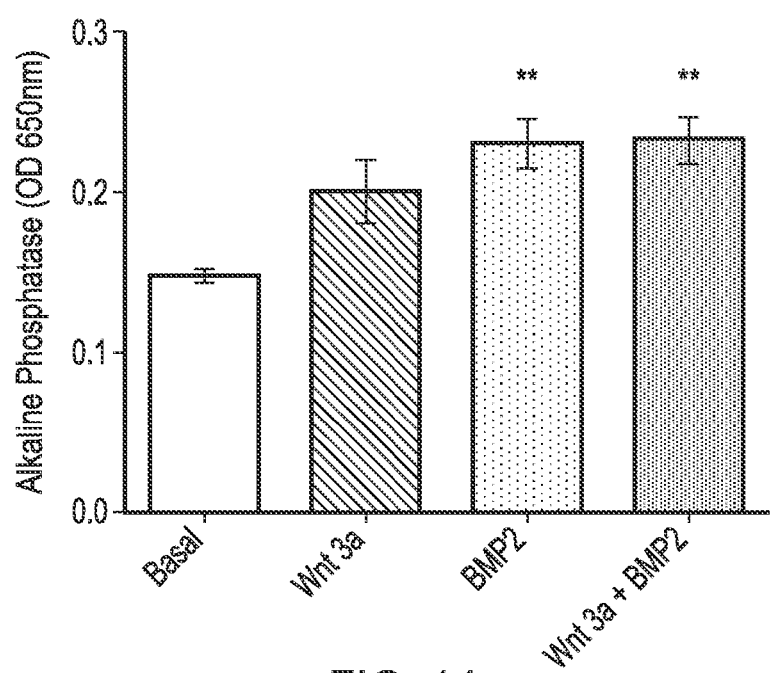
FIG. 14 shows the amount of alkaline phosphatase detected in cultures of MG 63 cells grown on Wnt 3a and BMP2-functionalised cell culture surface. The cells were cultured on the functionalised surfaces for 14 days in basal medium in the absence of serum or additional growth factors. Results are the means+/−SEM.

Scaffolds were functionalised with example osteogenic bioactive factors Wnt3a, BMP2 and a combination of both growth factors. FIG. 14 shows the effect of the functionalised scaffolds on alkaline phosphatase in MG 63 cells. Scaffolds functionalised with BMP2 showed a statistically significant increase in alkaline phosphatase levels. Wnt 3a showed some increase in alkaline phosphatase which did not reach statistical significance. Together with the cell viability data, scaffolds functionalised with osteogenic factors supported the survival of ligamentocytes, MSCs and MG 63 osteoblastic cells. Therefore, in summary, scaffolds functionalised with appropriate osteogenic factors could have utility in promoting regeneration of bone, ligament and related tendon tissues. In particular, use of appropriate bioactive factors could promote regeneration of the bone-ligament or bone-tendon insertion points (entheses) at which a tendon or ligament are often damaged by trauma.

Example 8

Figure 15A:
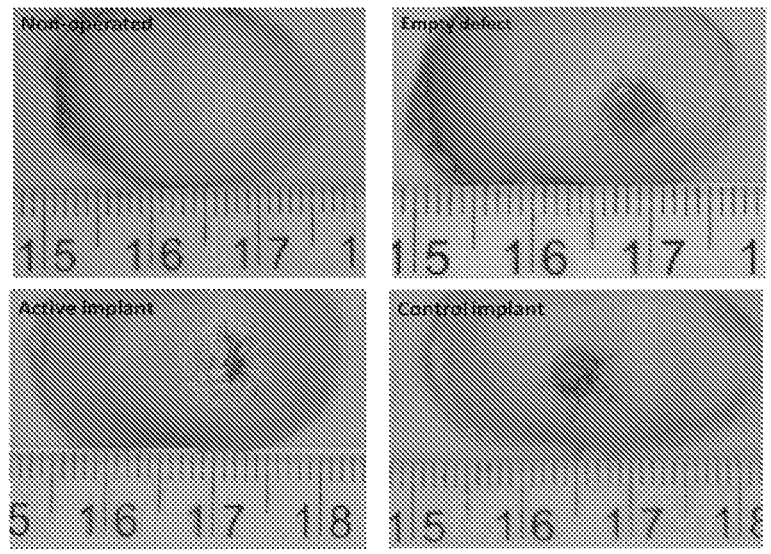
FIG. 15A shows photographs of an example non-operated contralateral femoral condyle, a femoral condyle with empty chondral defect, and a femoral condyle with a chondral defect treated with a control implant (PLLA functionalised with heparin only), a femoral condyle with a chondral defect treated with an active implant (PLLA functionalised with CXCL12 and TGFβ3).
Figure 15B:
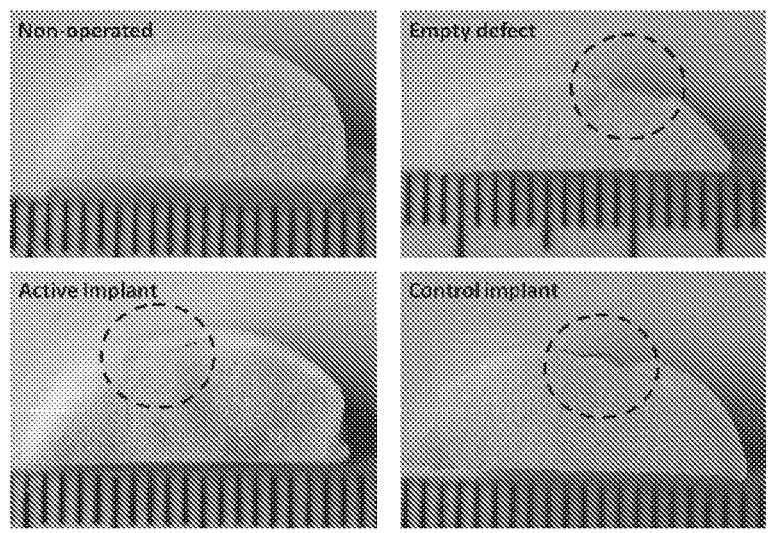
FIG. 15B shows photographs of a mid-sagittal section taken through the chondral defects of the partially decalcified condyles. The defects treated with the active implant (PLLA functionalised with CXCL12 and TGFβ3) show a greater volume of cartilage-like tissue regeneration.

FIG. 15 shows examples of gross morphology of example sheep femoral condyles retrieved at post-mortum 28 days after surgery. FIG. 15A shows photographs of an example non-operated contralateral femoral condyle, a femoral condyle left with an unfilled/empty chondral defect, and a femoral condyle with a chondral defect treated with a control implant (PLLA functionalised with heparin only) and a femoral condyle with a chondral defect treated with an 'active' implant (PLLA functionalised with CXCL12 and TGFβ3). FIG. 15B shows the sagittal sections taken through the defects to show the volume of articular tissue regeneration. It can be seen that there is greater regeneration of the cartilage layer in the defects treated with the 'active' (CXCL12 and TGFβ3-functionalised PLLA) implants vs the empty defects or defects treated with the control (heparin-functionalised) implant. This cartilage tissue regeneration was greater in area (FIG. 15A) and volume (FIG. 15B) with the 'active' implants We have demonstrated that PLLA functionalised with CXCL12 and TGFβ3 can regenerate articular cartilage to a greater degree than leaving the defect empty/unfilled or implanting a scaffold functionalised with heparin only. In summary, these results show that appropriate bioactive factor—functionalised scaffolds (such as CXCL12 and TGFβ3-functionalised PLLA) can have in vivo functionality to promote articular cartilage regeneration.

Example 9

Figure 16:
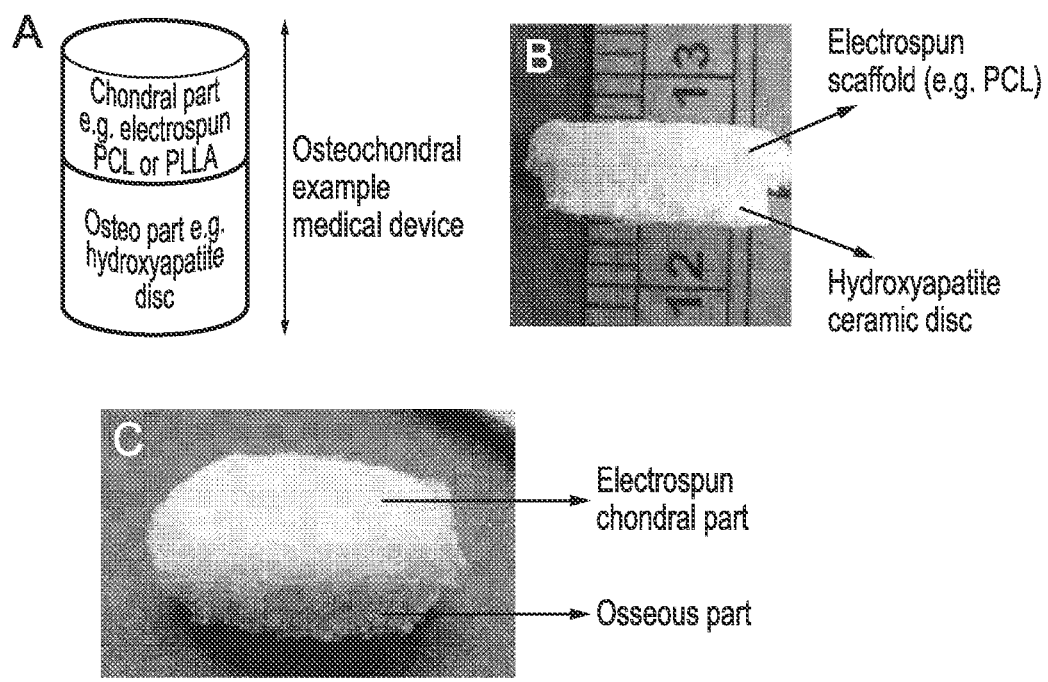
FIG. 16 shows the components of an example osteochondral device.
Figure 16:
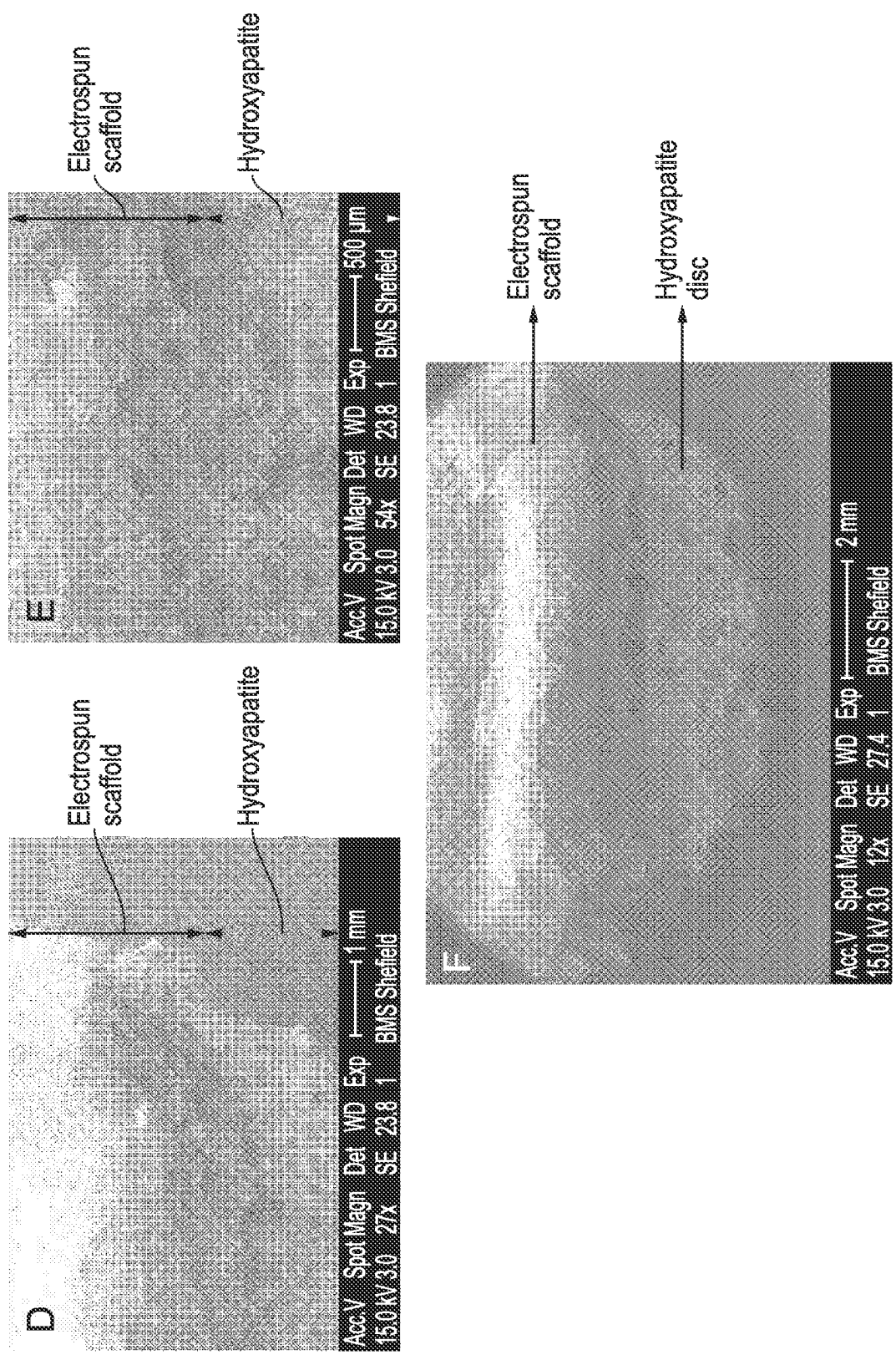

FIG. 16 shows the general design principles of an osteochondral implant. The diagram (not to scale) shown in FIG. 16A shows the basic components of an osteochondral implant. In this device, the chondral portion would be composed of a biological factor-functionalised scaffold as described herewithin. The osseous part could be formed by deposition of hydroxyapatite or brushite onto one end of an electrospun scaffold by for example, an alternative soaking technique[62]. Or a chondral scaffold could be attached to a suitable osseous scaffold or by heat annealing or using a biological adhesive (for example, fibrin sealant) Alternatively, a chondral portion could be directly electrospun onto an osseous scaffold as exemplified in FIGS. 16B and 16C which show photographs of an osteochondral medical device comprised of a hydroxyapatite disc osseous region onto which was electrospun a 1.8 mm random-fibre scaffold of polycaprolactone (PCL) to form the chondral portion. After fabrication the scaffold portions could be functionalised with appropriate bioactive factors as described herewithin. FIGS. 16D, 16E and 16F are scanning electron micrographs of the PCL chondral portion which was directly electrospun (depth 1.8 mm) onto the osseous scaffold (1 cm ceramic disc) of hydroxyapatite. Use of the osteochondral implant should enable better fixation and stabilisation of the implant in some clinical indications (e.g. large osteoarthritic lesions, or large full-depth lesions extending into the subchondral bone caused by trauma) compared to using just the functionalised chondral scaffold.

Additionally, the results of the biological factor-functionalised scaffolds on chondrocyte function would suggest that scaffolds functionalised with suitable BFs could have utility as the biomaterial support used for matrix-assisted autologous chondrocyte implantation (MACI) which is a procedure which is used clinically although not currently available on the NHS.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

REFERENCES

1. Abramson S B, Attur M and Yazici Y, Prospects for disease modification in osteoarthritis. (2006). *Nat. Clin. Pract. Rhematol.* 2: 304-312.
2. Goldring M B and Goldring S R. Osteoarthritis. (2007). *J Cellular Physiol.* 213:626-634.
3. Abramson S B and Attur M. Developments in the scientific understanding of osteoarthritis. (2009). *Arthritis Res. & Therapy* 11: 227-236.
4. Leardini G, Salaffi F, Caporali R, Canesi B, Rovati L, Montanelli R. Direct and Indirect costs of osteoarthritis. (2004). *Clin. Exp Rheumatol.* 22: 699-706.
5. National Institute for Health and Clinical Excellence (NICE). (2008). 'Osteoarthritis: The care and management of osteoarthritis in adults'. Clinical Guideline. 59.
6. Simon T M and Jackson, T W. Articular cartilage injury pathways and treatment options. (2006). *Sports Med Arthrosc.* 14: 146-154.
7. Laurpattarakasem W, Laopaiboon M, Laurpattarakasem P, Sumananont C. Arthroscopic debridement for knee osteoarthritis. (2008). *Cochrane Database of Systematic Reviews.* DOI:10.1002/14651858.CD005118.pub2.
8. Simon T M and Jackson, T W. Articular cartilage injury pathways and treatment options. (2006). *Sports Med Arthrosc.* 14: 146-154.
9. Messner K, Gillquist J. Cartilage repair: a critical review. (1996). *Acta Orthop Scand* 67:532-539.
10. Gidwani S and Fairbank A. The orthopedic approach to managing osteoarthritis of the knee. (2004). *Br Med J* 329: 1220-1224.
11. Sampson S, Botto-van Bemden A, Aufiero D. Autologous bone marrow concentrate: review and application of a novel intra-articular orthobiologic for cartilage disease. (2013). *Phys Sports Med* 41 (3): 7-18.
12. Roos E M. Joint injury causes knee osteoarthritis in young adults. (2005). Current Opinion Rheumatol. 17: 195-200.

13. National Institute for Health and Clinical Excellence (NICE). (2005). 'The use of autologous implantation for the treatment of cartilage defects in knee joints'. Review of Technology Appraisal 16. www.nice.org.uk
14. Guidance on the selection of prostheses for primary total hip replacement. (2000). *Technology Appraisal Guidance—No. 2. National Institute for Clinical Excellence.* www.nice.org.uk
15. Fisher J. Surgery for arthritis: total hip and knee joint replacement. (2004). Reports on the Rheumatic Diseases Series 5: Topical Reviews. *Arthritis Research UK.* www.aruk.org.uk.
16. Kim K T, Lee S, Ko D O, et al. Causes of failure after total knee arthroplasty in osteoarthritis patients 55 years of age or younger. (2014) *Knee Surg Relat Res* 26: 13-19.
17. Aggarwal V K, Goyal N, Deirmengian G, et al. Revision total knee arthroplasty in the young patient: is there trouble on the horizon? (2014) *J Bone Joint Surg Am* 96: 536-542.
18. Steadman J R, Rodkey W G, Rodrigo J J. Microfracture: surgical technique and rehabilitation to treat chondral defects. (2001). *Clin OrthopRel Res* 391(suppl):S362-S369.
19. Peterson L, Minas T, Brittberg M, Nilsson A, Sjorgenson-Jansson E. and Lindahl A. Two to 9-year outcome after autologous chondrocyte transplantation. (2000). *Clin Orthop Relat Res* 374: 212-234.
20. Minas T. and Peterson L. Advanced techniques in autologous chondrocytes transplantation. (1999) *Clin Sports Med.* 18: 13-44.
21. Trattnig S, Ba-Salamah A, Pinker K, Plank C, Vecsei V and Marlovits S. Matrix-based autologous chondrocytes implantation for cartilage repair: non-invasive monitoring by high resolution magnetic resonance imaging. (2005). *Man Reson Imaging* 23: 779-787.
22. Clar C, Cummins E, McIntyre L, Thomas S, Lamb J, Bain L, Jobanputra P and Waugh N. Clinical and cost effectiveness of autologous chondrocyte implantation for cartilage defects in knee joints: systematic review and economic evaluation. (2005). *Health Technology Assessment* 9: no 47.
23. Waisiak J, Clar C and Villanueva E. Autologous cartilage implantation for full thickness cartilage defects of the knee. (2006). *Cochrane Database of Systemic Reviews.* Issue 3, article no: CD003323.
24. Ruano-Ravina, A and Diaz M J. Autologous chondrocyte implantation: a systemic review. (2006). *Osteoarthritis & Cartilage* 14: 47-51.
25. Jones E A, Crawford A, English A, Henshaw K, Mundy J, Corscadden D, Chapman T, Emery P, Hatton P V, McGonagle, D. Synovial Fluid mesenchymal stem cells in health and early osteoarthritis: Detection and functional evaluation at the single-cell level. (2008). *Arthritis & Rheumatism.* 58: 1731-1740.
26. Van der Kraan P M, Buma P, van Kuppevelt, van den Berg W. Interaction of chondrocytes, growth factors: relevance for tissue engineering. (2002). *Osteoarthritis and Cartilage* 10: 631-637.
27. Lotolf M P and Hubbell J A. Synthetic biomaterials as instructive microenvironments for morphogenesis in tissue engineering. (2005). *Nature Biotech.* 23: 47-55.
28. Kim S-H, Turnbull J, Guimond S. Extracellular matrix and cell signalling: the dynamic cooperation of integrin, proteoglycan and growth factor receptor. (2011). *J. Endocrinol.* 209: 130-151.
29. Knox S M, Whitelock J M. Perlecan: How does one molecule do so many things? (2006). *Cell Mol Life Sci.* 63(21): 2435-2445.
30. Rapraeger A C., Syndecan-regulated receptor signalling. (2000). *J Cell Biol.* 149(5): 995-997.
31. Lortat-Jacob H. The molecular and functional implications of chemokine interactions with heparin sulphate. (2009). *Current Opin. Structural Biol.* 19: 543-548.
32. Kufareva I, Salanga C L, Handel T M. Chemokine and chemokine receptor structure and interactions: implications for therapeutic strategies. (2015). *Immun Cell Biol* 93:372-383.
33. Raman R, Sasisekharan V, Sasisekharan R. Structural insights into biological roles of protein-glycosaminoglycan interactions. (2005). *Chemistry and Biology* 12(3): 267-277.
34. Zern B J, Chu Hh and Wang Y D. Control growth factor release using self-assembly [polycation:heparin] complex. (2010). *Plos One* 5(6): e11017.
35. Brown A, Robinson C J, Gallagher J T, Blundell I L, Co-operative heparin-mediated oligomerisation of fibroblast growth factor-1 (FGF-1) precedes recruitment of FGR2 to ternary complexes. (2013). *Biophys. J* 104: 1720-1730.
36. Chen G, Gulbranson D R, Yua P, Houa Z, Thomson J A. Thermal stability of fibroblast growth factor protein is a determinant factor in regulating self-renewal, differentiation and reprogramming in human pluripotent stem cells. (2012). *Stem Cells* 30(4): 623-630.
37. Laguri C, Arenzana-Seisdedos F, Lortat-Jacob H. Relationships between glycosaminoglycan and receptor binding sites in chemokines—the CXCL12 example. (2008). *Carbohydrate Research* 343: 2018-2023.
38. Pomin V H, Mulloy B. Current structural biology of the heparin interactome. (2015). *Current Opinion in Structural Biology* 34:17-25
39. Proudfoot A E, Handel T M, Johnson Z, Lau E K, LiWang, P, Clark-Lewis I, Borlat F, Wells T N, Kosco-Vilbois M H. Glycosaminoglycan binding and oligomerization are essential for the in vivo activity of certain chemokines. (2003). *Proc. Natl. Acad. Sci.* 100: 1885-1890
40. Tscheudschilsuren G, Bosserhoff A K, Schlegel J, Vollmer D, Anton A, Alt V, Schnettler, R, Brandt J, Proetzel G. Regulation of stem cell and chondrocyte differentiation by MIA. (2006). *Exp. Cell. Res.* 312: 63-72.
41. Stoll R, Renner C, Zweckstetter M, Brüggert M, Ambrosius D, PALme S, Engh R A, Golob M, Breibach I, Buettner R, Voelter W, Holak T A, Bosserhoff A-K. The extracellular human melanoma inhibitory activity (MIA) protein adopts an SH3 domain-like fold. *The EMBO J.* 20: 340-349
42. Hileman R E, Fromm J R, Weiler J M, Lindhardt R J. Glycosaminoglycan-protein interactions: definition of consensus sites in glycosaminoglycan binding proteins. (1998). *Bioassays* 20(2): 156-157.
43. Sun T, Mai S M, Norton D, Haycock J W, Ryan A J, MacNeil S. Self-organisation of skin cells in three-dimensional electrospun polystyrene scaffolds. (2005). *Tissue Engineering* 11: 1023-1033.
44. Xu X, Jha A K, Duncan R L. Heparin-decorated, hyaluronic acid-based hydrogel particles for the controlled release of bone morphogenic protein 2. (2011). *Acta Biomater.* 7: 3050-3059.

45. Vulic K, Shoichet M S. Tunable growth factor delivery from injectable hydrogels for tissue engineering. (2011). *J. Am. Chem. Soc.* 134: 882-885.
46. Volpato F Z, Almodovar J, Erickson K, Popat K, Migliaresi, C, Kipper M J. Preservation of FGF-2 bioactivity using heparin-based nanoparticles, and their delivery from electrospun chitosan fibers. (2012). *Acta Biomater.* 8: 1551-1559.
47. Chen M X, Li B K, Yin D K, Liang J, Peng D Y. Layer-by-layer assembly of chitosan stabilized multilayered liposomes for paclitaxel delivery. (2014). *Carbohydrate Polymers* 111: 298-304.
48. Manakhov A, Nečas D, Čechal J, Pavliňák D, EliášM, Zajičková L. Deposition of stable amine coating onto polycaprolactone nanofibers by low pressure cyclopropylamine plasma polymerization. (2015). *Thin Solid Films* 581: 7-13.
49. Yasuda H and Gazicki M. Biomedical applications of plasma polymerization and plasma treatment of polymer surfaces. (1982). *Biomaterials* 3: 68-77.
50. Mahoney D J, Whittle J D, Milner C M, Clark S J, Mulloy B, Buttle D J, Jones G C, Day A J. Short R D. A method for the immobilization of heparin to surfaces. (2004). *Anal. Biochem.* 330: 123-129.
51. Short R, Buttle D, and Day A. Sugar binding surface. (2002) PCT/GB2003/004653 (WO/2004/040308).
52. Robinson D E, Marson A, Short R D, Buttle D J, Day A J, Parry K, Wiles M, Highfield P, Mistry A. Whittle J. Surface gradient of functional heparin. (2008). *Advanced Materials,* 20: 1166-1169
53. Robinson D E, Buttle D J, Short R D, McArthur S L, Steele D A, Whittle J D. Glycosaminoglycan (GAG) surfaces for characterising GAG-protein interactions. (2012). *Biomaterials* 334:1007-1016.
54. CN 101269240 'Artificial crystalline lens with transforming growth factor resistant beta 2 antibody membrane on surface manufacturing method thereof'
55. Crawford A, Dickinson S C. Chondrocyte isolation, expansion and culture on polymer scaffolds. (2004). *Methods in Molecular Biology* 238:147-158.
56. Rider C C. Heparin/heparan sulphate binding in the TGF-beta cytokine superfamily. (2006). *Biochem Soc Trans.* 34(Pt 3):458-60.
57. Lyon M, Rushton G, Gallagher J T. The interactions of transforming growth factor β with heparin/heparin sulphate. (1997). *J Biol Chem.* 272:18000-18006.
58. McCaffrey T A, Falcone D J, Viicente D, Du B. Transforming growth factor-beta 1 is a heparin-binding protein: identification of putative heparin-binding regions and isolation of heparins with varying affinity for TGF-beta 1. (1992). *J Cell Physiol.* 152:430-440.
59. Freeman I, Cohen S. The influence of sequential delivery of angiogenic factors from affinity-binding alginate scaffolds on vascularisation. (2009). *Biomaterials* 30: 2122-2131.
60. US 2013/0251683 A1. Prolonged Delivery of Heparin-binding Growth Factors from Heparin-Derivatized Collagen. (2013).
61. Ferndale R W, Buttle D J, Barrett A J. Improved quantitation and improved discrimination of sulphated glycosaminoglycans by use of dimethylmethylene blue. (1986). *Biochimia et Biphysica Acta* 883: 173-177.
62. Tagushi T, Kishida A, Akashi M. Apatite formation on/in hydrogel matrices using an alternative soaking process: II Effect of swelling ratios of poly(vinyl alcohol) hydrogel matrices on apatite formation. (1999) *J Biomaterials Polymer Science-Polymer Edition,* 10: 331-339.

The invention claimed is:
1. An acellular biomimetic medical device comprising a scaffold coated in or adsorbed on its surfaces with a first layer comprising a cationic agent, the first layer being covered or coated with a second layer comprising an anionic oligosaccharide or polysulphated moiety, which is non-covalently bound to a mixture of a plurality of bioactive factors, wherein the plurality of bioactive factors comprises:
 (i) an agent that can stimulate stem cell differentiation and/or promote appropriate extracellular matrix formation for the tissue to be regenerated selected from the transforming growth factor β group; and
 (ii) a stem cell homing or migratory factor which is a chemokines and optionally
 (iii) an agent that inhibits enzymes associated with the breakdown or catabolism of extracellular matrix.
2. The device according to claim 1, wherein the first and second layers are non-covalently bound together.
3. The device according to claim 1, wherein the scaffold is synthetic, natural, and/or selected from the group comprising polyester compositions, polylactic acid, polylactic acid-glycolic acid copolymer compositions, polycaprolactone, polyester-polyallylamine copolymers, collagens, peptides, silks, chitosan, hyaluronan-based polymers, decellularized tissue, calcium phosphate-based materials, hydroxyapatite and ceramic based biomaterials and combinations and compositions of the foregoing scaffold materials with ceramic based biomaterials.
4. The device according to claim 1, wherein the cationic agent is a stable unsaturated amine or is allylamine.
5. The device according to claim 1, wherein the second layer comprises an anionic oligosaccharide or a sulphated moiety.
6. The device according to claim 5, wherein the anionic oligosaccharide is selected from the group comprising heparin and heparan sulphate, dermatan sulphate, chondroitin-4-sulphate, chondroitin-6-sulphate, hyaluronic acid, hyaluronan, keratan sulphate and pentosan polysulphate and oligosaccharides derived from any of the above.
7. The device according to claim 1, wherein the bioactive factor is bound to the anionic material either directly, indirectly, or indirectly via a linker moiety.
8. The device according to claim 7, wherein the linker moiety is selected from the group comprising fibronectin, insulin-growth factor binding protein, vitronectin and laminin and peptide derivatives thereof.
9. The device according claim 1, wherein the chemokine is selected from the group consisting of CXCL12, SDF1β, CCL2 (MCP-1), CCL21, CXCL1, and CXCL8 (IL8), and optionally wherein the agent that inhibits enzymes associated with the breakdown or catabolism of extracellular matrix is selected from the group consisting of tissue inhibitor of metalloproteinase-3, osteoprotegerin, Wnt proteins such as Wnt 3a, DNA complexes, DNA plasmid/viral complexes, complexes of RNA, microRNA and derivatives or biologically active fragments thereof.
10. The device according to claim 1, wherein the stem cell homing or migratory factor is CXCL12.
11. The device according to claim 1, wherein the plurality of bioactive factors are sequestered at levels in the nanogram/picomole range.
12. The device according to claim 1, further including a surface modification to include a bioactive agent that enhances osteogenic function-or a treatment which promotes deposition of hydroxyapatite particles to create an osseous region on the device.

13. The device according to claim 1, further which is an osteochondral device purposed to aid implant fixation for the regeneration of articular cartilage and underlying subchondral bone which may be fabricated of different biomaterials composing the chondral and osseous regions.

14. A method of making the device of claim 13, comprising electrospinning a chondral scaffold onto an osseous scaffold or by physically attaching a chondral portion to an osseous region.

15. A method of constructing the acellular biomimetic medical device of claim 1, comprising:
(i) providing a scaffold core;
(ii) coating a surface of the scaffold core or impregnating the surface of the scaffold core with a first layer comprising a cationic agent;
(iii) covering the first layer of with a second layer comprising an anionic oligosaccharide or polysulphated moiety; and
(iv) attaching a mixture of a plurality of bioactive factors non-covalently either directly to said second layer or indirectly via a linker moiety to said second layer, wherein the plurality of bioactive factors comprises:
a) an agent that can stimulate stem cell differentiation and/or promote appropriate extracellular matrix formation for the tissue to be regenerated selected from the transforming growth factor β group; and
b) a stem cell homing or migratory factor which is a chemokine; and optionally
c) an agent that inhibits enzymes associated with the breakdown or catabolism of extracellular matrix.

16. The method according to claim 15, wherein the scaffold comprises a non-woven porous material.

17. The method according to claim 15, wherein the surface of the scaffold core is coated or covered with the first layer comprising the cationic agent by plasma polymerisation.

18. A method of promoting mesenchymal stem cell differentiation into an appropriate cell type for tissue regeneration and/or promoting appropriate extracellular matrix formation and/or inhibiting enzymes associated with the breakdown or catabolism of extracellular matrix or the cartilage matrix and/or encouraging stem cell homing into a tissue defect to promote tissue regeneration and/or treating or promoting healing of an injured joint surface, or an early osteoarthritic lesion, and promoting healing of bone, meniscal cartilage, tendon and/or ligament injuries in a subject in need thereof, the method comprising implanting the device according to claim 1 into an area of a joint or other area of the subject.

19. The method according to claim 18, wherein the joint is a synovial joint.

20. The method according to claim 16, wherein the material is electrospun poly-L-lactic acid or polyglycolic acid-poly-L-lactic acid co-polymers or polycaprolactone polymers.

21. The device according to claim 1, wherein the agent that can stimulate stem cell differentiation and/or promote appropriate extracellular matrix formation for the tissue to be regenerated is TGFβ3.

* * * * *

UNITED STATES PATENT AND TRADEMARK OFFICE
CERTIFICATE OF CORRECTION

PATENT NO. : 10,765,779 B2
APPLICATION NO. : 15/747410
DATED : September 8, 2020
INVENTOR(S) : Crawford-Corrie et al.

It is certified that error appears in the above-identified patent and that said Letters Patent is hereby corrected as shown below:

On the Title Page

(56) References Cited, OTHER PUBLICATIONS, Page 2, Column 2, Line 38, Steadman et al. cite: Please correct "5362-5369" to read -- S362-S369 --

In the Specification

Column 17, Line 47: Please correct "(FIGSS.)" to read -- (FIGS.) --

Column 19, Line 5: Please correct "p≤3.01" to read -- p≤0.01 --

Column 23, Line 23: Please correct "5362" to read -- S362 --

Column 25, Line 47: Please correct "Viicente" to read -- Vicente --

In the Claims

Column 26, Line 14, Claim 1: Please correct "chemokines" to read -- chemokine; --

Column 26, Line 53, Claim 9: Please correct "of tissue" to read -- of: tissue --

Signed and Sealed this
Sixteenth Day of February, 2021

Drew Hirshfeld
*Performing the Functions and Duties of the
Under Secretary of Commerce for Intellectual Property and
Director of the United States Patent and Trademark Office*